(12) United States Patent
Imamura et al.

(10) Patent No.: US 10,925,555 B2
(45) Date of Patent: Feb. 23, 2021

(54) RADIATION IMAGING APPARATUS, AND METHOD AND PROGRAM FOR CONTROLLING RADIATION IMAGING APPARATUS

(71) Applicant: FUJIFILM Corporation, Tokyo (JP)

(72) Inventors: Ryo Imamura, Ashigarakami-gun (JP); Kouichi Kitano, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 488 days.

(21) Appl. No.: 15/147,966

(22) Filed: May 6, 2016

(65) Prior Publication Data

US 2016/0331334 A1 Nov. 17, 2016

(30) Foreign Application Priority Data

May 11, 2015 (JP) .............................. JP2015-096282
Apr. 1, 2016 (JP) .............................. JP2016-073816

(51) Int. Cl.
*A61B 6/06* (2006.01)
*A61B 6/00* (2006.01)

(52) U.S. Cl.
CPC .............. *A61B 6/06* (2013.01); *A61B 6/4283* (2013.01); *A61B 6/465* (2013.01); *A61B 6/467* (2013.01); *A61B 6/587* (2013.01); *A61B 6/4488* (2013.01)

(58) Field of Classification Search
CPC ......... A61B 6/587; A61B 6/06; A61B 6/4283; A61B 6/4488; A61B 6/465; A61B 6/467
See application file for complete search history.

(56) References Cited

U.S. PATENT DOCUMENTS

| 5,077,778 A | * | 12/1991 | Fabian | G03B 42/047 378/162 |
| 2005/0118532 A1 | * | 6/2005 | Mallmann | G03F 9/7084 430/311 |
| 2006/0219926 A1 | * | 10/2006 | Shoji | H04N 5/3415 250/370.09 |
| 2008/0034257 A1 | * | 2/2008 | Hilderscheid | G06F 11/006 714/46 |

(Continued)

FOREIGN PATENT DOCUMENTS

| JP | 2005-261844 A | 9/2005 |
| JP | 2007-29353 A | 2/2007 |

(Continued)

OTHER PUBLICATIONS

Machine translation of JP2013111216 (Year: 2013).*

(Continued)

*Primary Examiner* — Dani Fox
*Assistant Examiner* — Soorena Kefayati
(74) *Attorney, Agent, or Firm* — Sughrue Mion, PLLC

(57) ABSTRACT

A radiation imaging apparatus includes: a radiation irradiating apparatus that emits radiation onto a subject; a photography unit that photographs the subject to obtain a photographed image of the subject; and a radiation detector that generates radiation images of the subject, provided with a marker that represents identifying information of the radiation detector on the side thereof that includes a radiation detecting surface. The marker of the radiation detector is detected. The identifying information of the radiation detector is obtained from a marker in the case that the marker is detected.

8 Claims, 14 Drawing Sheets

(56) References Cited

U.S. PATENT DOCUMENTS

| | | | |
|---|---|---|---|
| 2008/0063249 A1* | 3/2008 | Ohtsuka | A61B 6/4283 382/131 |
| 2009/0022276 A1* | 1/2009 | Ohara | A61B 6/4233 378/101 |
| 2009/0103796 A1* | 4/2009 | Akagi | G16H 30/40 382/132 |
| 2009/0136000 A1* | 5/2009 | Nishii | A61B 6/5235 378/98.3 |
| 2009/0218497 A1* | 9/2009 | Nishino | A61B 6/4216 250/362 |
| 2009/0220049 A1* | 9/2009 | Nishino | A61B 6/5294 378/98.2 |
| 2009/0257564 A1* | 10/2009 | Kito | A61B 6/587 378/206 |
| 2009/0272907 A1* | 11/2009 | Hara | A61B 6/0487 250/370.09 |
| 2011/0069814 A1* | 3/2011 | Yonekawa | A61B 6/4494 378/62 |
| 2011/0075817 A1* | 3/2011 | Takahashi | A61B 6/547 378/189 |
| 2011/0249791 A1* | 10/2011 | Wang | A61B 6/547 378/62 |
| 2012/0195407 A1* | 8/2012 | Nenoki | G03B 42/047 378/98.5 |
| 2013/0168564 A1* | 7/2013 | Konkle | G01T 1/00 250/370.09 |
| 2013/0301802 A1* | 11/2013 | Eguchi | H05G 1/08 378/98 |
| 2015/0131782 A1* | 5/2015 | Park | A61B 6/4411 378/62 |
| 2015/0157289 A1* | 6/2015 | Park | H04W 72/0406 600/407 |
| 2016/0148398 A1* | 5/2016 | Takemoto | A61B 6/5264 378/63 |
| 2016/0324664 A1* | 11/2016 | Piron | A61B 5/1072 |
| 2017/0135667 A1* | 5/2017 | Becker | A61B 6/4464 |
| 2018/0220989 A9* | 8/2018 | Deinlein | A61B 6/4464 |

FOREIGN PATENT DOCUMENTS

| | | |
|---|---|---|
| JP | 2009-34428 A | 2/2009 |
| JP | 2009028374 A | 2/2009 |
| JP | 2009-131323 A | 6/2009 |
| JP | 2010-119485 A | 6/2010 |
| JP | 2013111216 * | 6/2010 |
| JP | 2012-152461 A | 8/2012 |
| JP | 2013-524477 A | 6/2013 |
| JP | 2013-236711 A | 11/2013 |
| JP | 2015-77251 A | 4/2015 |
| WO | 2014/128757 A1 | 8/2014 |

OTHER PUBLICATIONS

Office Action dated Jul. 16, 2019 in Japanese Application No. 2018-174994.

Communication dated Dec. 3, 2019 from the Japanese Patent Office in application No. 2018-174994.

* cited by examiner

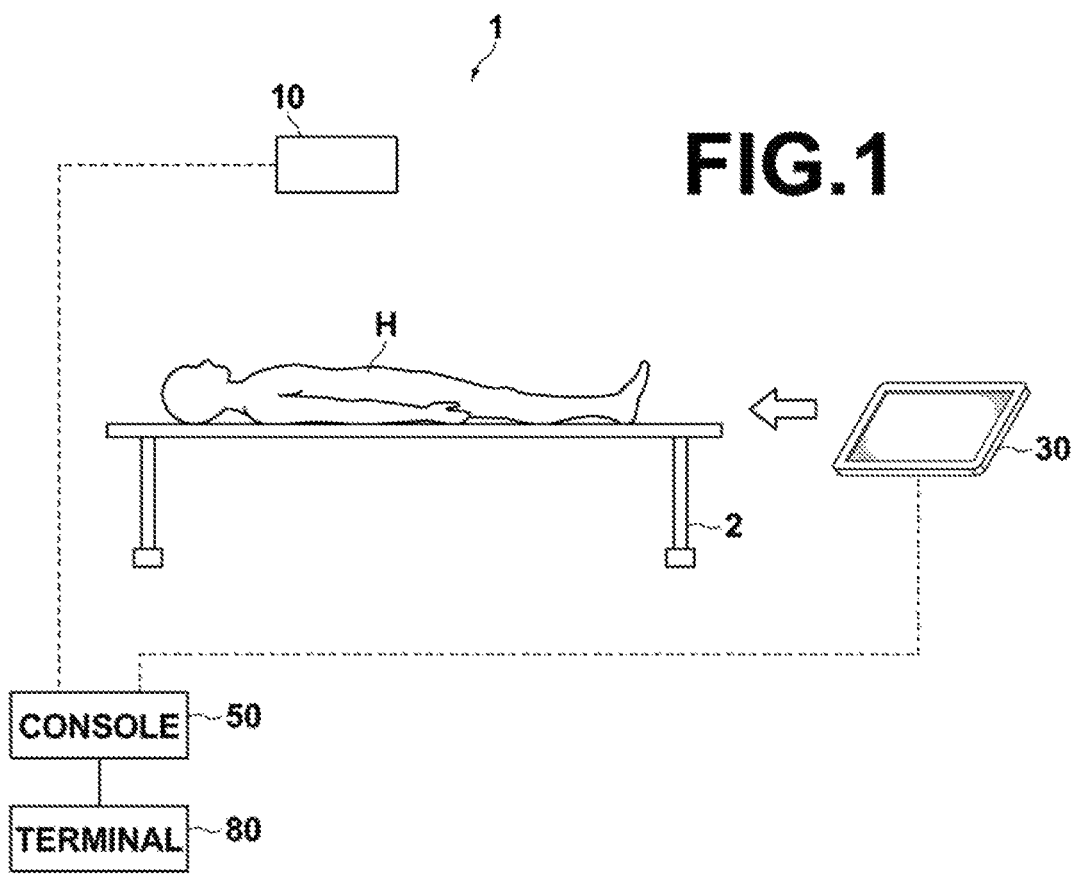
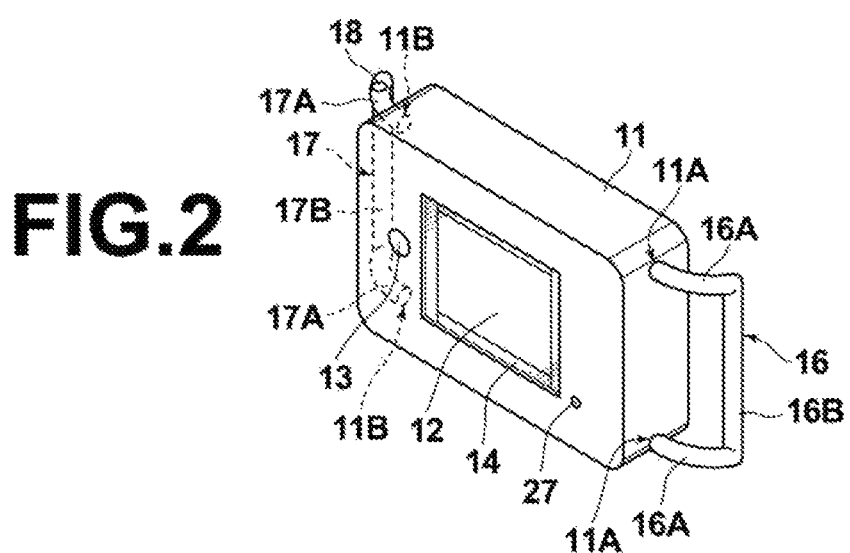

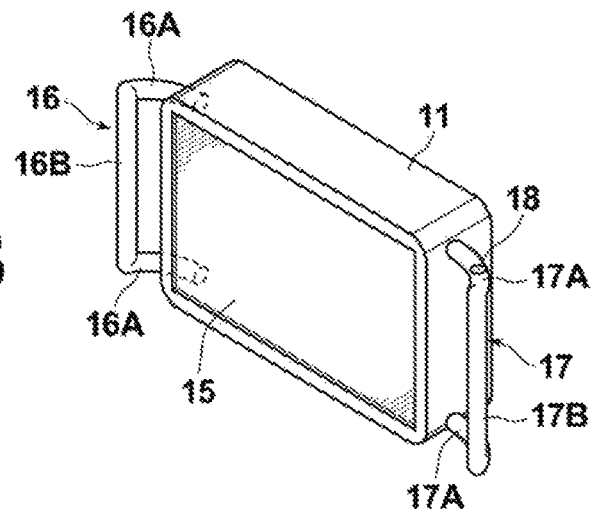
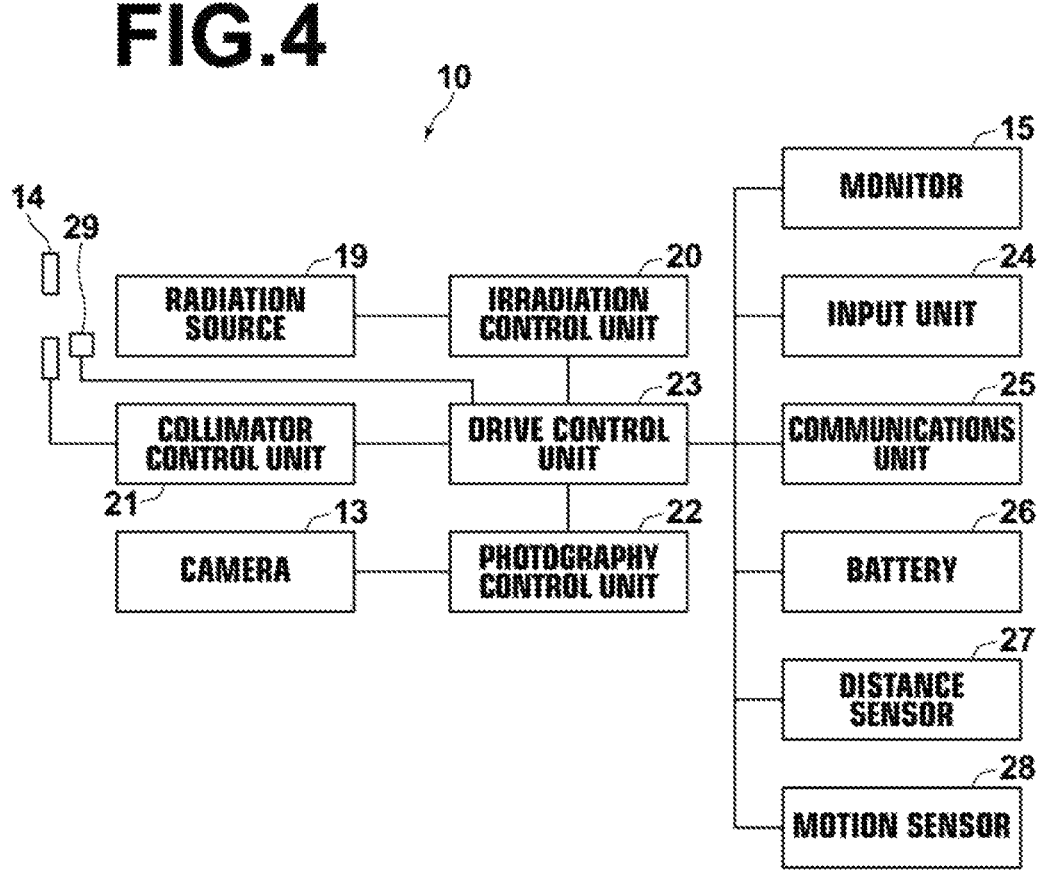

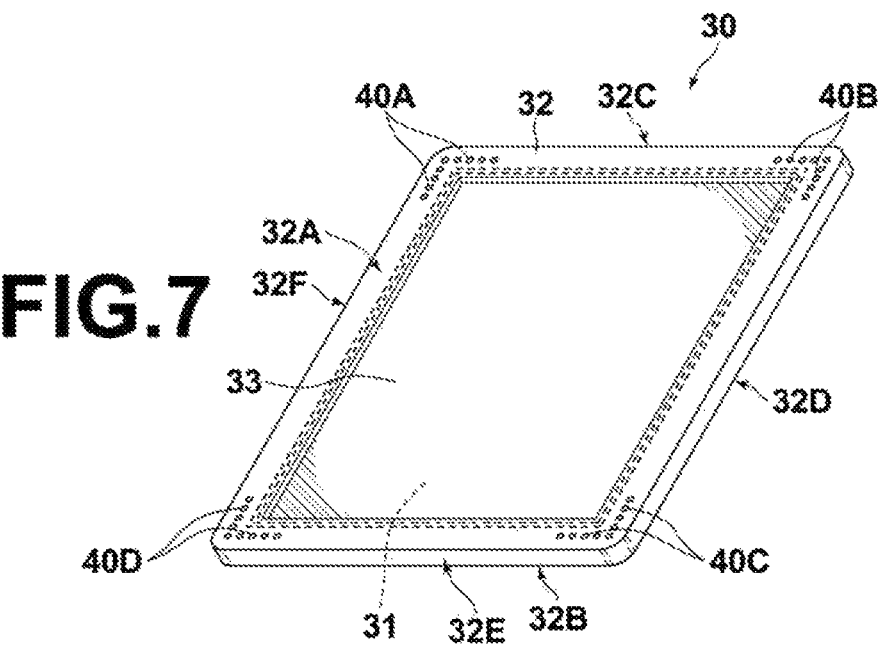
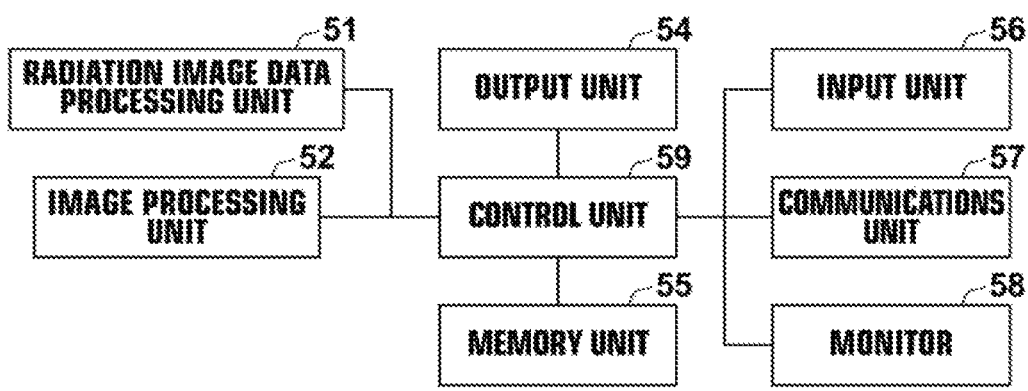

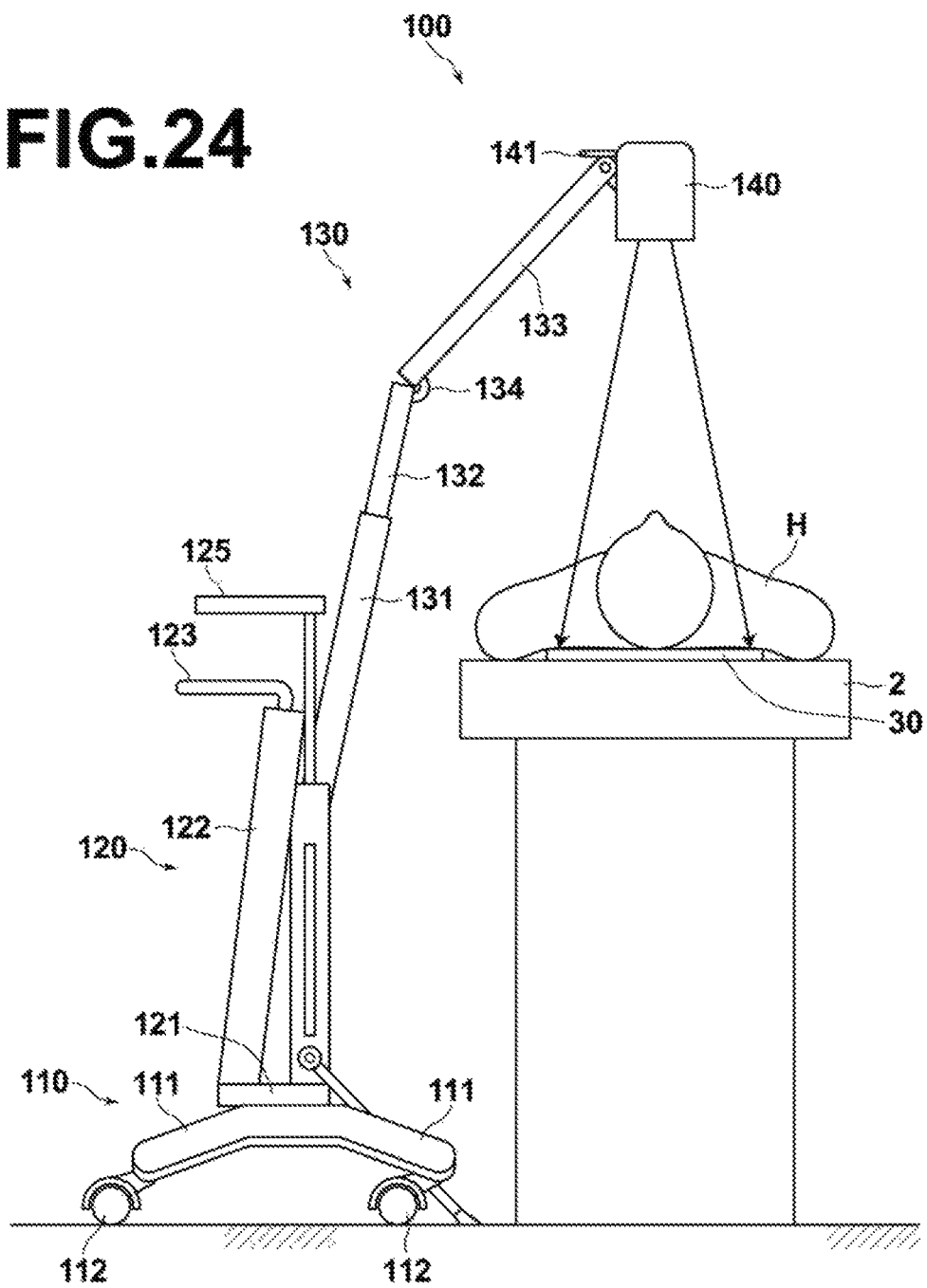

RADIATION IMAGING APPARATUS, AND METHOD AND PROGRAM FOR CONTROLLING RADIATION IMAGING APPARATUS

CROSS REFERENCE TO RELATED APPLICATIONS

The present application claims priority under 35 U.S.C. § 119 to Japanese Patent Application No. 2015-096282 filed on May 11, 2015 and Japanese Patent Application No. 2016-073816 filed on Apr. 1, 2016. Each of the above applications is hereby expressly incorporated by reference, in its entirety, into the present application.

BACKGROUND

The present disclosure is related to a radiation imaging apparatus that obtains radiation images of subjects, as well as a method and program for controlling a radiation imaging apparatus.

Conventionally, various radiation imaging apparatuses that employ movable radiation irradiating apparatuses are known, as disclosed in Japanese Unexamined Patent Publication Nos. 2009-131323, 2007-029353, and 2010-119485. This type of radiation imaging apparatus employs a radiation irradiating apparatus for making patient rounds, which basically has a leg portion capable of movement by being provided with wheels, a main body portion that houses a battery for driving a radiation source and electric circuits for driving the radiation source, held above the leg portion, an arm portion linked to the main body portion, and a radiation source mounted on the arm portion, to emit radiation onto subjects.

In addition, a radiation imaging apparatus that employs a portable radiation irradiating apparatus equipped with the bare minimum components for irradiating radiation, which are a radiation source, electric circuits, etc., which is operated manually by an operator, has also been proposed. The weight of this type of portable radiation irradiating apparatus is reduced to a degree that enables an operator to hold and operate the radiation irradiating apparatus manually. This type of portable radiation irradiating apparatus is capable of finer maneuvering during imaging.

When obtaining a radiation image of a subject using such a radiation imaging apparatus, generally, a radiation detector (a so called "flat panel detector") that records a radiation image that represents the subject formed by radiation which has passed through the subject and is irradiated thereon, is utilized. As such a radiation detector, the cassette type radiation detector, which is formed by an image detecting unit, a battery for driving the detector, and a control unit constituted by electric circuits for driving the detector, etc., housed within a box, is well known. Such a radiation detector is positioned to face a radiation irradiating apparatus with the subject interposed therebetween, and the radiation irradiating apparatus is driven in this state. Thereby, radiation which has passed through the subject is irradiated onto the radiation detector, and a radiation image represented by radiation which has passed through the subject is obtained.

In addition, an imaging method has been proposed for radiation imaging apparatuses in which the aforementioned radiation irradiating apparatus and the radiation detector are separate components. In this method, a subject is imaged with a camera to obtain a photographed image that represents the surface of the subject, which is displayed, in order to confirm an irradiation field (refer to Japanese Unexamined Patent Publication Nos. 2009-131323, 2007-029353, and 2010-119485). In addition, shifts are likely to occur between the irradiation field of radiation and the detection range of a radiation detector, in radiation imaging apparatuses in which the aforementioned radiation irradiating apparatus and the radiation detector are separate components. For this reason, Japanese Unexamined Patent Publication Nos. 2009-131323, 2007-029353, and 2010-119485 also propose a method in which a frame that indicates the irradiation field of radiation and a frame that indicates the detection region of a radiation detector are overlapped and displayed on the displayed photographed image.

In order to display the detection region of a radiation detector on a photographed image in this manner, it is necessary to detect the position of the radiation detector. For this reason, a technique has been proposed in which markers, RF signals, combinations of reflective elements and light or electromagnetic signals, etc. are employed to detect the position of a radiation detector. Then, the detection region of the radiation detector is overlapped and displayed on a photographed image, based on the detected position (refer to PCT Japanese Publication No. 2013-524477).

Radiation detectors are comparatively costly. For this reason, a radiation detector is not prepared in each hospital room during rounds when imaging is performed in a plurality of hospital rooms, but a radiation detector is brought to each hospital room along with a radiation irradiating apparatus, and utilized to obtain radiation images. A console for controlling imaging operations is prepared in each hospital room, and radiation detectors to be utilized are registered in each console. Meanwhile, radiation detectors are provided with unique identifying information. During imaging operations, the identifying information of a radiation detector to be utilized is input to a console. The console employs the identifying information to judge whether the radiation detector to be utilized is a radiation detector which has been registered. When it is confirmed that the radiation detector to be utilized is a radiation detector which has been registered, wireless or wired communication is performed between the radiation detector and the console, to exchange radiation images and various types of data. The identifying information is input to the console by connecting the console and the radiation detector with a cable and transmitting the identifying information, by an operator directly inputting the identifying information of the radiation detector into the console, or by inputting the identifying information into the console using a remote control or the like.

SUMMARY

However, it is extremely troublesome to connect a radiation detector to a console or to input the identifying information of a radiation detector to a console each time that imaging operations are performed.

The present disclosure has been developed in view of the foregoing circumstances. The present disclosure provides a radiation imaging apparatus that obtains radiation images of subjects, as well as a method and program for controlling a radiation imaging apparatus that facilitate input of identifying information of a radiation detector.

A radiation imaging apparatus according to the present disclosure comprises:

a radiation source that emits radiation onto a subject;

a photography means for photographing the subject to obtain a photographed image of the subject; and an identifying information obtaining means for detecting a marker, provided on a radiation detector that detects radiation which has passed through the subject and generates a radiation image of the subject, that represents identifying information of a radiation detector, the marker being provided on the side of the radiation detector that includes a radiation detecting surface, and obtaining the identifying information of the radiation detector from the marker in the case that the marker is detected.

The "photographed image of the subject" is an image that represents the surface of the subject and objects in the periphery thereof, within a photography range of the photography means. Note that an infrared image that represents the temperature distributions of the surface of the subject and the surfaces of objects in the periphery thereof, obtained by photographing the subject using infrared rays, is also included as a referent of the "photographed image of the subject".

Note that in the radiation imaging apparatus according to the present disclosure, the radiation source and the photography means may be provided as an integrated unit.

The expression "provided as an integrated unit" means that the radiation source and the photography means are provided as an integral and inseparable unit. For example, a configuration in which the radiation source and the imaging means are provided in the same chassis is that in which the radiation source and the imaging means are provided as an integrated unit.

In addition, the radiation imaging apparatus according to the present disclosure may further comprise an identifying means for identifying the radiation detector based on the identifying information.

In addition, in the radiation imaging apparatus according to the present disclosure, the marker may be provided at a portion at the side of the detecting surface other than a detection region that detects radiation.

The expression "a portion at the side of the detecting surface other than a detection region that detects radiation" may be a portion within a frame at the periphery of the detection region that detects radiation of the radiation detector.

In addition, in the radiation imaging apparatus according to the present disclosure, a surface of the radiation detector that includes the detection region that detects radiation may be of a rectangular shape, and each of a plurality of markers may be provided at least at one of the vicinities of different edges and the vicinities of different corners of the surface that includes the detection region.

The expression "vicinities" means that the markers are provided close to at least one of the edges and the corners of the rectangular surface that includes the detection region. Specifically, the markers may be in contact with at least one of the edges and the corners or may be separated from at least one of the edges of the corners, to a degree that does not inhibit detection of radiation by the surface that includes the detection region.

In addition, in the radiation imaging apparatus according to the present disclosure, the marker may be a bar code. Note that the bar code may be linear or two dimensional.

In addition, in the radiation imaging apparatus according to the present disclosure, the marker may be that which represents different types of radiation detectors using different colored information as the identifying information.

In addition, in the radiation imaging apparatus according to the present disclosure, the marker may be a light emitting device, and the identifying information may be represented by at least one of the color of light, the lighting pattern of the light, and the blinking pattern of the light emitted by the light emitting device.

In addition, in the radiation imaging apparatus according to the present disclosure, at least one of the color of light, the lighting pattern of the light, and the blinking pattern of the light emitted by the light emitting device may represent detector information of the radiation detector.

In addition, the radiation imaging apparatus according to the present disclosure may further comprise a positional relationship obtaining means for obtaining the relative positional relationship between the radiation detector and the radiation source based on at least one of the size and the shape of a marker within the photographed image, in the case that the marker is detected.

In addition, in the radiation imaging apparatus according to the present disclosure, the surface of the radiation detector opposite the detecting surface may be provided with another marker that represents that the surface is that which is opposite the detecting surface.

A method for controlling a radiation imaging apparatus of the present disclosure is a method for controlling a radiation imaging apparatus equipped with a radiation source that irradiates radiation onto a subject and photography means for photographing the subject to obtain a photographed image of the subject, comprising:

detecting a marker that represents identifying information of a radiation detector that detects radiation which has passed through the subject and generates a radiation image of the subject, provided on the side of the radiation detector at the side of a radiation detecting surface, from the photographed image; and obtaining the identifying information of the radiation detector from a marker in the case that the marker is detected.

Note that the method for controlling a radiation imaging apparatus of the present disclosure may be provided as a program that causes a computer to execute the method.

According to the present disclosure, the marker of the radiation detector is detected from the photographed image, and identifying information of the radiation detector is obtained from the marker in the case that the marker is detected. Thereby, identifying information of a radiation detector can be input into a console or the like, simply by photographing the radiation detector using the photography means. Accordingly, the burden of operations to input identifying information of a radiation detector into a console on an operator can be reduced.

BRIEF DESCRIPTION OF THE DRAWINGS

FIG. 1 is a schematic diagram that illustrates a radiation imaging apparatus according to an embodiment of the present disclosure.

FIG. 2 is a front side perspective view of a radiation irradiating apparatus.

FIG. 3 is a rear side perspective view of the radiation irradiating apparatus.

FIG. 4 is a schematic block diagram that illustrates the inner components of the radiation irradiating apparatus.

FIG. 7 is a perspective view of a radiation detector which is provided with an LED as a marker as viewed from the front surface, onto which radiation is irradiated.

FIG. 8 is a schematic block diagram that illustrates the inner components of a console.

FIG. 24 is a side view that illustrates the radiation irradiating apparatus configured to be capable of movement in a state of use.

DETAILED DESCRIPTION OF THE EMBODIMENTS

Figure 5:
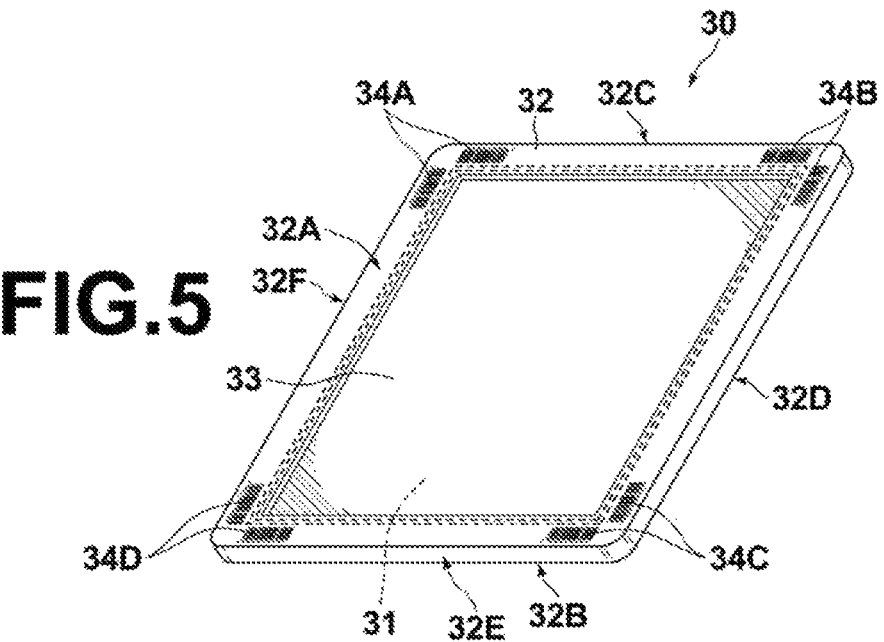
FIG. 5 is a perspective view of a radiation detector as viewed from the front surface, onto which radiation is irradiated.

Hereinafter, embodiments of the present disclosure will be described with reference to the attached drawings. FIG. 1 is a schematic diagram that illustrates a radiation imaging apparatus according to an embodiment of the present disclosure. As illustrated in FIG. 1, the radiation imaging apparatus 1 according to the present embodiment is equipped with a portable radiation irradiating apparatus 10, a radiation detector 30, and a console 50. In order to obtain a radiation image of a subject H who is lying on a bed 2, the radiation detector 30 is inserted between the subject H and the bed 2. Then, radiation is irradiated from the portable radiation irradiating apparatus 10 toward the subject H, and the radiation detector 30 obtains a radiation image of the subject H. In addition, the console 50 is connected to a terminal 80 of a physician or the like via a network.

FIG. 2 is a front perspective view of the radiation irradiating apparatus, FIG. 3 is a rear perspective view of the radiation irradiating apparatus, and FIG. 4 is a schematic block diagram that illustrates the inner components of the radiation irradiating apparatus. As illustrated in these drawings, the radiation irradiating apparatus 10 is constituted by an emission window 12, through which radiation is emitted, provided on the front surface of a rectangular parallelepiped chassis 11, a camera 13 for photographing the surface of the subject H, and a distance sensor 27. Note that a collimator 14 for narrowing the irradiation range of radiation can be viewed through the emission window 12. In addition, a monitor 15 constituted by liquid crystals or the like is provided on the rear surface of the chassis 11. The monitor 15 displays a photographed image obtained by the camera 13 photographing the surface of the subject H, the radiation image of the subject H, various pieces of information for setting the radiation irradiating apparatus 10, etc. The distance sensor 27 measures the distance between the apparatus 10 and a target object using a laser beam or ultrasonic waves. Note that the camera 13 and the monitor 15 respectively correspond to a photography means and a display means.

Grip portions 16 and 17 are respectively mounted on each of the two side surfaces of the chassis 11. The grip portion 16 is constituted by two protrusive portions 16A that protrude toward the side direction from the upper and lower portions of the side surface of the chassis 11, and a linking portion 16B that connects the two protrusive portions 16A. The grip portion 17 is constituted by two protrusive portions 17A that protrude toward the side direction from the upper and lower portions of the other side surface of the chassis 11, and a linking portion 17B that connects the two protrusive portions 17A. The protrusive portions 16A and 17A curve toward the rear surface of the chassis 11 from protruding portions 11A and 11B thereof. Note that instead of being curved, the protrusive portions 16A and 17A may be obliquely inclined toward the rear surface of the chassis 11 from the protruding portions 11A and 11B. An operator can move the radiation irradiating apparatus 10 to a position at which it is possible to photograph the subject H, by holding the grip portions 16 and 17. Note that an imaging button 18 that causes radiation to be emitted to image the subject H is provided on the upper protruding portion 17A of the grip portion 17, which is to be held by the right hand of an operator when performing imaging operations.

The chassis 11 houses the monitor 15, a radiation source 19, an irradiation control unit 20, a collimator control unit 21, a photography control unit 22, a drive control unit 23, an input unit 24, a communications unit 25, a battery 26, the distance sensor 27, a motion sensor 28, and an irradiation field lamp 29. By adopting this configuration, the radiation source 19 and the camera 13, which is the photography means 13, are provided as an integrated unit. Note that the irradiation control unit 20, the collimator control unit 21, the photography control unit 22, the drive control unit 23, and the communications unit 25 are configured by a program (software) that operates in a computer, dedicated hardware, or a combination of the two. Note that the program may be distributed by being recorded on a recording medium such as a DVD (Digital Versatile Disc) or a CD-ROM (Compact Disc Read Only Memory), and installed into the radiation irradiating apparatus 1—from the recording medium. Alternatively, the program may be stored in a storage device of a server computer connected to a network, or stored in a network storage in a state accessible from the exterior, downloaded to the radiation irradiating apparatus 10 in response to requests, then installed therein.

The radiation source 19 is constituted by an X ray bulb, a boosting circuit, a cooling means for cooling the X ray bulb, etc., for example.

The irradiation control unit 20 drives the radiation source 19 and controls the dosage of radiation irradiated onto the subject H such that radiation of an intensity corresponding to imaging conditions which are set in advance is irradiated onto the subject H for a set amount of time. The imaging conditions are a bulb voltage (kV value) corresponding to the body thickness of the subject H, and an mAs value (bulb current×irradiation time). Note that the body thickness of the subject can be obtained by measuring SID (Source Image receptor Distance), which is the distance between the apparatus 10 and the surface of the radiation detector 30, and SOD (Source Object Distance), which is the distance between the apparatus 10 and the surface of the subject H, then subtracting SOD from SID. Note that alternatively, the operator may measure the body thickness and input information for setting imaging conditions that include the measured body thickness into the apparatus 10 via the input unit 24. In the present embodiment, information for setting imaging conditions such as the body thickness is transmitted to the console 50, the console 50 sets the imaging conditions, and the set imaging conditions are transmitted to the radiation irradiating apparatus 10. The irradiation control unit 20 employs the imaging conditions transmitted thereto from the console 50 to control irradiation of radiation onto the subject H.

The collimator control unit 21 is constituted by a driving mechanism such as a motor for driving the collimator 14 to change the irradiation field of radiation which is irradiated onto the subject H from the radiation source 19, and electrical circuits and the like for controlling the driving mechanism. The collimator control unit 21 controls driving of the collimator 14 according to commands transmitted thereto from the drive control unit 23.

The photography control unit 22 drives the camera 13 to photograph the surface of the subject H and obtain a photographed image G1. In addition, the photography control unit 22 may administer image processes to improve the image quality of the photographed image G1 obtained by the camera 13. Note that the photographed image G1 is a video having a frame rate which is set in advance, for example, 30 fps.

The drive control unit 23 controls the driving of the entire radiation irradiating apparatus 10. That is, the drive control unit 23 performs a process of transmitting commands to the irradiation control unit 20 to drive the radiation source 19, a process of transmitting commands to the collimator control unit 21 to drive the collimator 14, a process of transmitting commands to the photography control unit 22 to drive the camera 13 and obtain a photographed image G1, a process of displaying various pieces of information including the photographed image G1 on the monitor 15, a process of transmitting commands to the communications unit 25 to exchange various types of information with the console 50, a process of monitoring the state of the battery 26, a process of receiving commands input through the input unit 24, a process of measuring the distance between the radiation irradiating apparatus 10 and a target object using the distance sensor 27, and a process of detecting movement of the radiation irradiating apparatus 10 using the motion sensor 28. Note that each of the above processes is performed according to commands input through the input unit 24 or according to commands transmitted by the console 50 and received by the communications unit 25.

The input unit 24 is that of a touch panel type which is integrated with the monitor 15. The input unit 24 receives commands from an operator and outputs data representing these commands to the drive control unit 23. Note that the imaging button 18 is also included in the input unit 24.

The communications unit 25 communicates wirelessly with the console 50 to exchange information therewith. Note that the radiation irradiating apparatus 10 and the console 50 may be connected by a cable and information may be exchanged in a wired manner instead of wirelessly. In the latter case, the communications unit 25 is equipped with a connector to which the cable is connected.

The motion sensor 28 is a nine axis motion sensor that detects acceleration along three axes, angular speed in three axes, and inclination in three axes. The acceleration, angular speed, and inclination detected by the motion sensor 28 are output to the drive control unit 23 as movement information and employed to control the radiation irradiating apparatus 10 during imaging. In addition, the movement information is transmitted to the console 50 from the communications unit 25. Note that the inclination is that which uses a position of the radiation irradiating apparatus 10 which is maintained horizontal in a state in which a radiation irradiation axis that matches the direction in which radiation is irradiated is aligned with the direction in which gravity operates as a reference position.

The irradiation field lamp 29 is constituted by a light emitting element that emits visible light, such as a light bulb or an LED (Light Emitting Diode). The drive control unit 23 controls the ON/OFF state of the irradiation field lamp 29. When the irradiation field lamp 29 is turned ON, visible light is irradiated onto an irradiation field on the subject H, onto which radiation will be irradiated.

Figure 6:
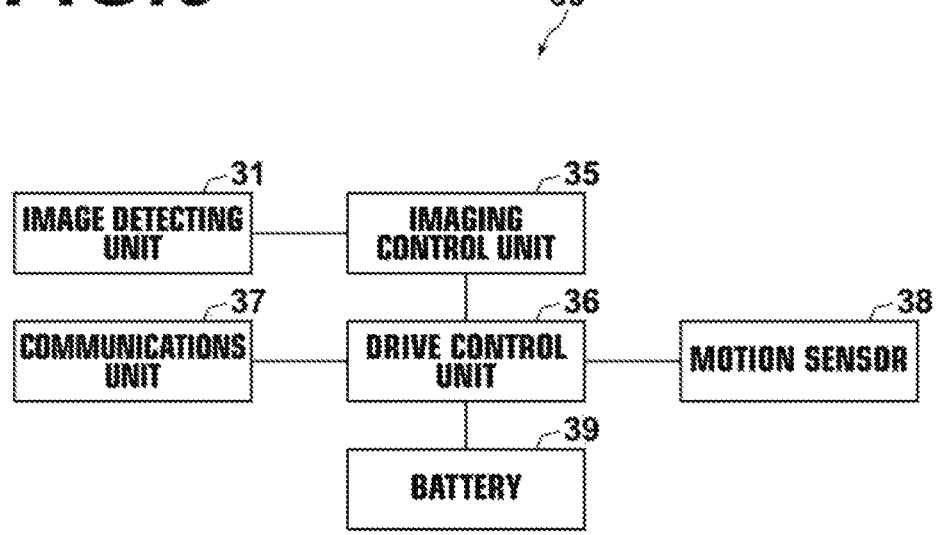
FIG. 6 is a schematic block diagram that illustrates the inner components of the radiation detector.

Next, the configuration of the radiation detector 30 will be described. FIG. 5 is a perspective view of the radiation detector 30 as viewed from the front surface, onto which radiation is irradiated. FIG. 6 is a schematic block diagram that illustrates the inner components of the radiation detector.

As illustrated in FIG. 5, the radiation detector 30 is a cassette type radiation detector equipped with a chassis 32 that houses an image detecting unit 31. The image detecting unit 31 is of a well known configuration and is equipped with scintillators (phosphors) that convert incident radiation into visible light and a TFT (Thin Film Transistor) active matrix circuit board. A rectangular imaging region, in which a plurality of pixels that accumulate electrical charges corresponding to the visible light from the scintillators are arranged, is formed on the TFT active matrix circuit board. The chassis 32 also houses an imaging control unit 35 equipped with a gate driver that provides gate pulses to TFT gates to switch the TFT's, a signal processing circuit that converts the electrical charges which are accumulated at the pixels into analog electrical signals that represent an X ray image and outputs the analog electrical signals, in addition to the image detecting unit 31.

The chassis 32 is of a rectangular parallelepiped shape having a front surface 32A, which is a detection surface into which radiation enters, a rear surface 32B opposed to the front surface 32A, and four side surfaces 32C, 32D, 32E, and 32F. The chassis 32 is formed by an electrically conductive resin, for example, and also functions as an electromagnetic shield that prevents entry of electromagnetic noise into the radiation detector 30 and radiation of electromagnetic noise from the interior to the exterior of the radiation detector 30. The chassis 32 is of a size which is approximately the same as that of film cassettes, IP (Imaging Plate) cassettes, or CR (Computed Radiography) cassettes, and complies with ISO (International Organization for Standardization) 4090:2001.

A transmitting plate 33 that transmits radiation is mounted on the front surface 32A of the chassis 32. The transmitting plate is of a size that substantially matches the detection region that detects radiation in the radiation detector 30, and is formed by a carbon material which is lightweight, has high rigidity, and high radiation transmissivity.

Markers 34A through 34D that represent identifying information for identifying the radiation detector 30 are provided at the four corners of the front surface 32A of the chassis 32. Here, information that represents at least one of an ID number that identifies individual radiation detectors 30, a manufacturing number, the size of the radiation detector 30, the type of the radiation detector 30, etc., may be employed as the identifying information. In the present embodiment, each of the markers 34A through 34D is a set of two linear bar codes that extend in directions that perpendicularly intersect each other. The sets of two bar codes are provided at portions of the front surface 32A of the radiation detector 30 other than the detection region so as to define the four corners of the detection region. Thereby, each of the markers 34A through 34D is provided in the vicinity of a different corner of the surface of the radiation detector 30 that includes the detection region. Note that markers that represent color information that differs according to types of radiation detectors may be employed, as long as such markers are capable of identifying the radiation detector 30. For example, tape having a color unique to the radiation detector 30 may be employed as a marker. In this case, the radiation detector 30 can be identified by the color of the marker.

Here, each of the markers 34A through 34D is constituted by a pair of bar codes. In the present embodiment, one of the two bar codes includes information that represents the vertical direction of the image detecting unit 31 which is housed in the radiation detector 30. In the present embodiment, the side at which the markers 34A and 34B are provided is designated as the upper side, that is, the top side. Accordingly, in the present embodiment, in the case that the edge along the side at which the markers 34A and 34B are provided and the edge along the side at which the markers 34C and 34D are provided are defined in the radiation detector 30, the direction from the edge along the side at which the markers 34C and 34D are provided to the edge along the side at which the markers 34A and 34B are provided along a line that perpendicularly intersects these edges is the top side direction. Note that the top side direction refers to a direction on the radiation detector 30, and does not refer to a direction along the direction in which gravity operates.

Note that a light emitting element such as an LED that emits light of a color unique to the radiation detector 30 may be employed as a marker. In this case, the radiation detector 30 can be identified by the color of the light emitting element. In addition, markers 40A through 40d, each of which is constituted by a plurality of light emitting elements, provided at the four corners of the detection region of the radiation detector 30 may be employed as illustrated in FIG. 7. In this case, the radiation detector 30 can be identified by at least one of the color of light, the lighting pattern of the light, and the blinking pattern of the light emitted by the light emitting elements. Note that the light emitting elements correspond to light emitting devices.

In addition, the marker is not limited to bar codes or light emitting elements. It is only necessary for the position of a marker to be detected within the photographed image G1. Symbols, letters, or the like may be employed as markers, for example.

The chassis 32 houses the image detecting unit 31, the imaging control unit 35, a drive control unit 36, a communications unit 37, a motion sensor 38, and a battery 39. Note that the image detecting unit 31, the imaging control unit 35, the drive control unit 36, and the communications unit 37 are configured by a program (software) that operates in a computer, dedicated hardware, or a combination of the two. Note that the program is installed in the radiation detector 30 in the same manner as the program of the irradiation irradiating apparatus 10.

As described above, the imaging control unit 35 is equipped with the gate driver, the signal processing circuit, etc. The imaging control unit 35 controls the driving of these components, generates analog image signals that represent a radiation image G2, and outputs the analog image signals to the drive control unit 36.

The drive control unit 36 controls the driving of the entirety of the radiation detector 30. That is, the drive control unit 36 performs a process of transmitting commands to the imaging control unit 35 to generate image signals that represent the radiation image G2, a process of transmitting commands to the communications unit 37 to exchange the image signals that represent the radiation image G2 and various types of information with the console 50, a process of detecting movement of the radiation detector 30 using the motion sensor 38, a process of monitoring the state of the battery 39, etc.

The communications unit 37 communicates wirelessly with the console 50 to exchange information therewith. Note that the radiation detector 30 and the console 50 may be connected by a cable and information may be exchanged in a wired manner instead of wirelessly. In the latter case, the communications unit 37 is equipped with a connector to which the cable is connected.

The motion sensor 38 is a nine axis motion sensor that detects acceleration along three axes, angular speed in three axes, and inclination in three axes. The acceleration, angular speed, and inclination detected by the motion sensor 38 are output to the drive control unit 36, and transmitted to the console 50 from the communications unit 37. Note that the inclination is that which uses a position in which the radiation detector 30 is held horizontal as a reference position.

FIG. 8 is a schematic block diagram that illustrates the inner components of the console. As illustrated in FIG. 8, the console 50 is equipped with a radiation image data processing unit 51, an image processing unit 52, an output unit 54, a memory unit 55, an input unit 56, a communications unit 57, a monitor 58, and a control unit 59. Note that the radiation image data processing unit 51, the image processing unit 52, an output unit 54, a memory unit 55, the input unit 56, the communications unit 57, and the control unit 59 are configured by a program (software) that operates in a computer, dedicated hardware, or a combination of the two. Note that the program is installed in the console 50 in the same manner as the program of the irradiation irradiating apparatus 10.

The radiation image data processing unit 51 administers data processes such as A/D conversion onto image signals that represent the radiation image G2 of the subject H, input from the radiation detector 30. The radiation image data processing unit 51 outputs digital radiation image data which has undergone the data processes and represents the radiation image G2.

The image processing unit 52 administers predetermined image processes on the radiation image data output by the radiation image data processing unit 51, using image processing parameters which are stored in the memory unit 55. Various types of image processes are capable of being executed by the image processing unit 52, including: correction of missing pixels and generating a missing pixel map in order to correct missing pixels; image calibration processes (correction of radiation image data using calibration data) such as offset correction, gain correction that employs a predetermined uniformly exposed image, and shading correction; a gradation correcting process; a density correcting process; a process that removes scattered rays caused by radiation which has passed through the subject H; data converting processes for converting the image data for display on the monitor and to be output as prints. The image processing unit 52 outputs radiation image data which has undergone such image processes.

The output unit 54 outputs the radiation image data which has undergone various image processes and is input thereto from the image processing unit 52. The output unit 54 is a printer that outputs the radiation image as prints or a storage device that records radiation image data, for example.

The memory unit 55 stores the sizes of the detection regions of radiation detectors 30, image processing parameters for image processes which are performed by the image processing unit 52, types of radiation detectors 30 in order to set imaging conditions, parameters corresponding to the body thicknesses of subjects H, various types of information which are necessary for processes to be performed by the console 50, etc. The memory unit 55 also stores radiation images G2 output from the image processing unit 52 as well as photographed images G1 transmitted from the radiation irradiating apparatus 10. The memory unit 55 may be a semiconductor memory or a recording medium such as a hard disk. In addition, the memory unit 55 may be built in to the console 50 or provided externally and connected to the console 50.

The input unit 56 is constituted by a keyboard or the like that performs various types of input into the console 50. Note that the input unit 56 may be a touch panel.

The communications unit 57 communicates wirelessly with the radiation irradiating apparatus 10 and the radiation detector 30 to exchange information therewith. Note that the console 50, the radiation irradiating apparatus 10, and the radiation detector 30 may be connected by a cable and information may be exchanged in a wired manner instead of wirelessly. In the latter case, the communications unit 57 is equipped with a connector to which the cable is connected.

The monitor 58 is constituted by a liquid crystal panel or the like, and displays various types of information related to the console 50, radiation images G2 transmitted from the radiation detector 30, photographed images G1 if necessary, etc.

The control unit 57 controls the driving of the entire console 50. That is, the control unit 57 performs a process of issuing commands to the radiation image data processing unit 51 to obtain radiation images G2, a process of issuing commands to the image processing unit 52 to administer image processes on the radiation images G2, a process of obtaining identifying information of radiation detectors 30 from any of detected markers 34A through 34D, a process of identifying radiation detectors 30 based on the identifying information, a process of detecting the position of radiation detectors within photographed images G1, a process of outputting radiation images G2 to the output unit 54, a process of issuing commands to the communications unit 57 to exchange various types of information with the radiation irradiating apparatus 10 and the radiation detector 30, a process of receiving input from the input unit 56, a process of displaying various types of information on the monitor, etc. Note that the control unit 59 corresponds to an identifying information obtaining means and an identifying means.

Figure 9:
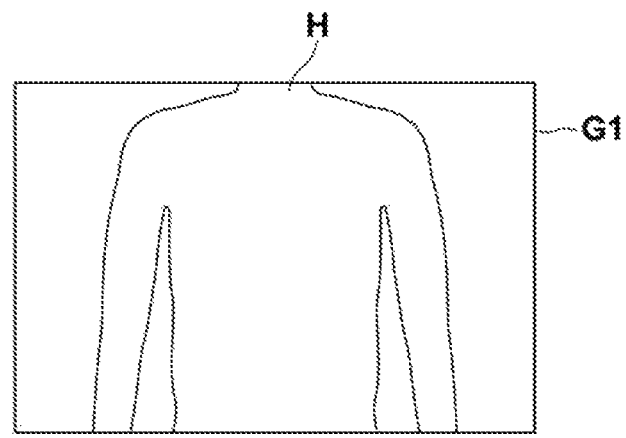
FIG. 9 is a diagram that illustrates a photographed image that only includes a subject.
Figure 10:
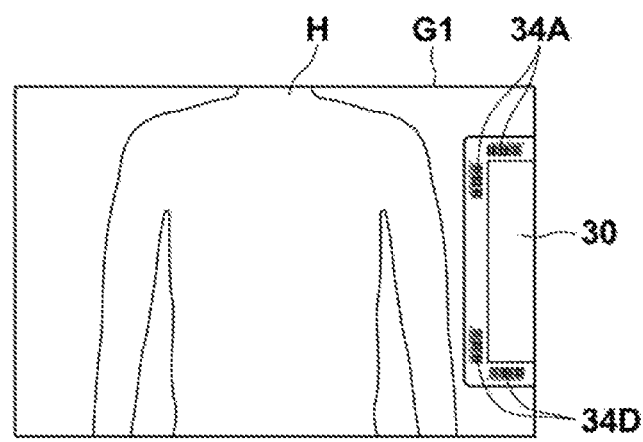
FIG. 10 is a diagram that illustrates a photographed image that includes a portion of a radiation detector in addition to a subject.

Hereinafter, detection of a radiation detector 30 in a photographed image G1 will be described. In the case that a radiation image of a subject H is to be obtained, an operator orients the radiation irradiating apparatus 10 toward the subject H, and photographs the subject H using the camera 13. In the present embodiment, the thorax of the subject H is to be imaged. For this reason, prior to imaging, a photographed image G1 includes the thorax of the subject H, as illustrated in FIG. 9. If an operation to insert the radiation detector 30 between the subject H and the bed in order to obtain a radiation image G2 of the subject H, the photographed image G1 includes a portion of the radiation detector 30, as illustrated in FIG. 10. Here, the radiation detector 30 is provided with markers 34A through 34D at the four corners thereof. The control unit 59 detects one of the markers 34A through 34D from the photographed image G1. If one of the markers 34A through 34D is detected within the photographed image G1, the control unit 59 judges that the photographed image G1 includes the radiation detector 30.

Meanwhile, the control unit 59 transmits radiation detector position information that represents the position of the radiation detector 30 within the photographed image G1 to the radiation irradiating apparatus 10. The radiation detector position information is a coordinate position that represents the positions of the corners of the detection region of the radiation detector within the photographed image G1. In the present embodiment, the size of the detection region of the radiation detector 30 is stored in advance in the memory unit 55. The control unit 59 obtains the radiation detector position information from the position of any one of the detected markers 34A through 34D and the size of the detection region. In addition, if the radiation detector position information is known, the center position of the radiation detector 30 can be calculated from the size of the detection region of the radiation detector 30. For this region, the control unit 59 also transmits center position information that represents the center position of the radiation detector 30 to the radiation irradiating apparatus 10. In addition, information regarding the vertical direction of the radiation detector 30 is identified from any one of the markers 34A through 34D, and information regarding the vertical direction is also transmitted to the radiation irradiating apparatus 10.

In addition, the control unit 59 obtains identifying information of the radiation detector 30 from any one of the markers 34A through 34D, in the case that one of the markers 34A through 34D is detected within the photographed image G1. In addition, the control unit 59 identifies the radiation detector employing the identifying information. Specifically, the control unit 59 judges whether the radiation detector 30 is a radiation detector that should be utilized. Here, the types of radiation detectors that should be utilized are registered in the console 50 in advance. That is, the identifying information of radiation detectors that should be utilized are recorded in the memory unit 55 as registered identifying information. The control unit 59 compares the identifying information of the radiation detector 30 against the registered identifying information stored in the memory unit 55, to judge whether the obtained identifying information is included in the registered identifying information. In the case that the result of this judgment is affirmative, the control unit transmits the identifying information to the radiation irradiating apparatus 10. The radiation irradiating apparatus displays the identifying information on the monitor 15, as will be described later. On the other hand, in the case that the result of this judgment is negative, the control unit 59 transmits information to the radiation irradiating apparatus indicating that the radiation detector 30 is not a radiation detector that should be utilized. The radiation irradiating apparatus 10 issues a warning indicating that the radiation detector 30 is not a radiation detector that should be utilized. Specifically, the radiation irradiating apparatus 10 displays text representing that the radiation detector 30 is not a radiation detector that should be utilized on the monitor 15. Thereby, the operator may take steps such as exchanging the radiation detector. Alternatively, the radiation detector 30 which is currently being utilized may be reregistered in the console. Thereby, an operation to exchange the radiation detector 30 can be obviated.

Figure 11:
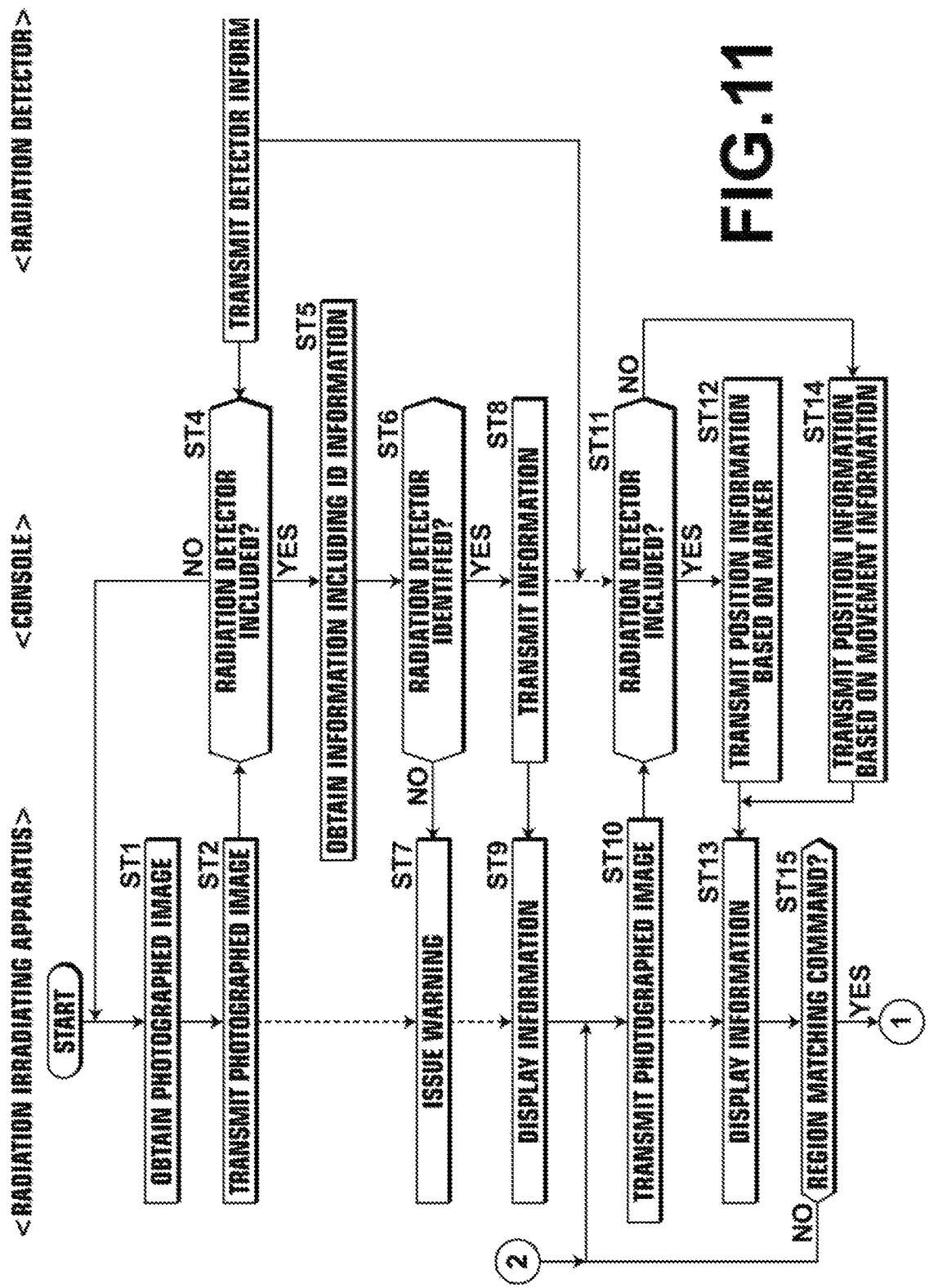
FIG. 11 is a flow chart that illustrates the processes which are performed by the present embodiment.
Figure 12:
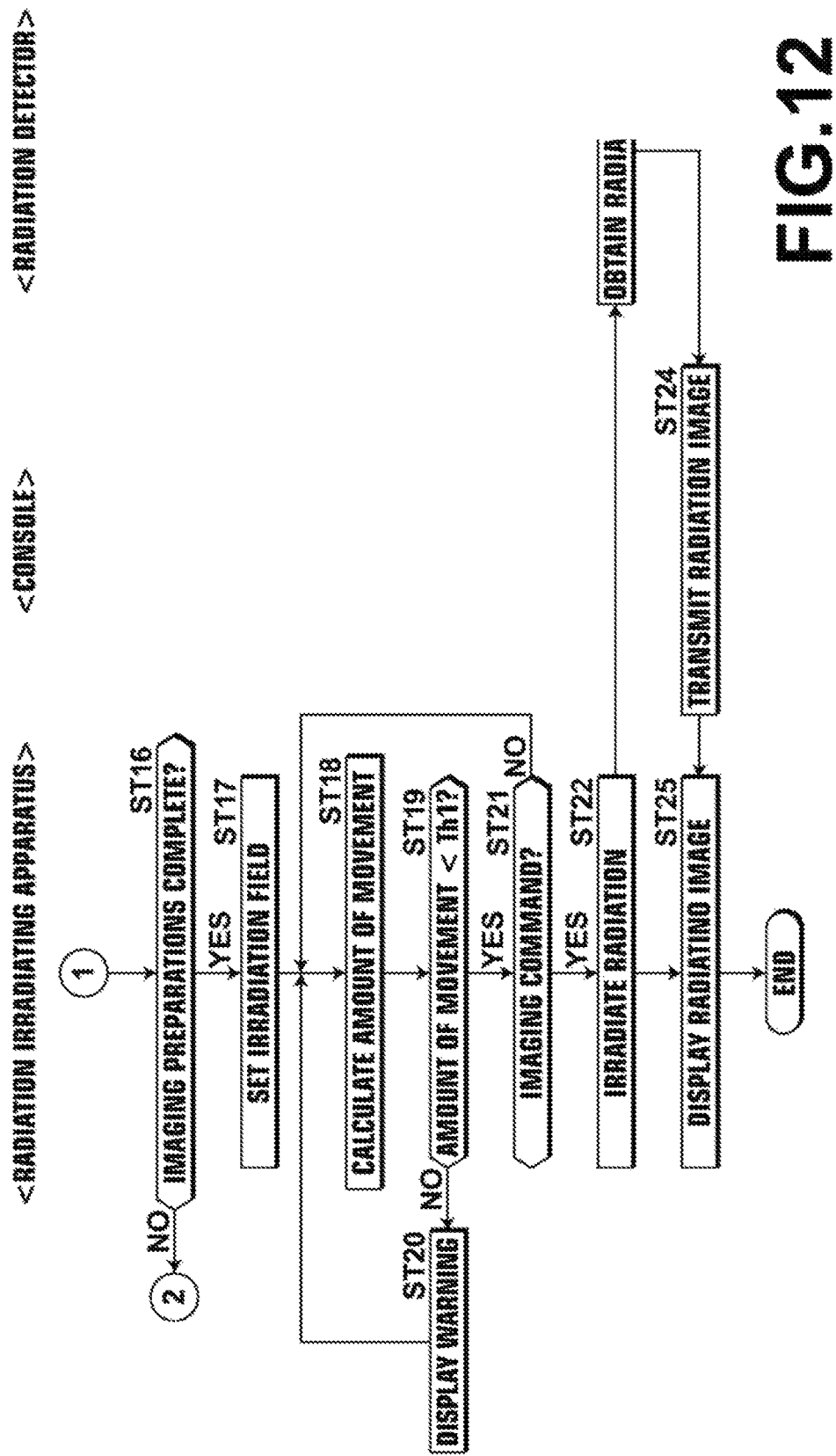
FIG. 12 is a flow chart that illustrates the processes which are performed by the present embodiment.

Next, the processes which are performed by the present embodiment will be described. FIG. 11 and FIG. 12 are flow charts that illustrate the processes which are performed by the present embodiment. Note that in the radiation imaging apparatus of the present embodiment, two operators respectively handle the radiation irradiating apparatus 10 and the radiation detector 30 to perform operations prior to imaging, such as positionally aligning the radiation detector 30 behind the subject H and setting the irradiation field. Imaging is performed following completion of the operations prior to imaging. First, the radiation irradiating apparatus 10 is held above the subject H, and the subject H is photographed by the camera 13, to obtain a photographed image G1 of the subject (step ST1). The radiation irradiating apparatus 10 transmits the photographed image G1, the SID, the SOD, and information regarding an irradiation field which is set by the collimator 14 to the console 50 (Transmission of Photographed Image, etc.: step ST2). In addition, the radiation detector 30 transmits information representing the driving state of the radiation detector 30, information representing the remaining battery power of the radiation detector 30, movement information detected by the motion sensor 38, etc., to the console (Detector Information Transmission: step ST3).

The control unit 59 of the console 50 detects any one of the markers 34A through 34D from the photographed image G1, to judge whether the photographed image includes a radiation detector 30 (step ST4). In the case that none of the markers 34A through 34D is detected within the photographed image G1 as illustrated in FIG. 9, and it is judged that the photographed image G1 does not include a radiation detector 30, the result of judgment at step ST4 is negative, and the process returns to step ST1. In the case that any one of the markers 34A through 34D is detected within the photographed image G1 as illustrated in FIG. 10, and it is judged that the photographed image G1 includes a radiation detector 30, the result of judgment at step ST4 is positive, and the control unit 59 obtains information related to the detector, which includes identifying information of the radiation detector 30, radiation detector position information that represents the position of the radiation detector 30 within the photographed image G1, information that represents the vertical direction of the radiation detector 30, and center position information of the radiation detector 30 (step ST5).

The control unit 59 identifies the radiation detector 30, by judging whether the obtained identifying information is identifying information of a radiation detector that should be utilized (step ST6). In the case that the obtained identifying information is not that of a radiation detector that should be utilized (step ST6: NO), the control unit transmits information indicating that the radiation detector 30 is not a radiation detector that should be utilized to the radiation irradiating apparatus 10. The radiation irradiating apparatus issues a warning indicating that the radiation detector 30 is not a radiation detector that should be utilized (step ST7). In the case that the obtained identifying information is that of a radiation detector that should be utilized (step ST6: YES), the process continues to step ST8.

Meanwhile, the control unit 59 calculates the body thickness of the subject H by subtracting SOD from SID, and sets imaging conditions based on the body thickness. Note that the imaging conditions may be set according to the portion of the subject H which is included in the photographed image G1. Information regarding the portion of the subject H may be obtained by the radiation irradiating apparatus 10 receiving operator input, or by the console 50 receiving input through the input unit 56 thereof. In addition, there are qualities of radiation (high voltage or low voltage) which are favorably suited for types of the scintillators which are utilized in the image detecting unit 31 housed within the radiation detector 30. For this reason, the imaging conditions may be set according to the material of the scintillators which are utilized in the image detecting unit 31 housed within the radiation detector 30, in addition to the body thickness. In this case, a table in which information regarding the scintillators which are utilized in the image detecting unit 31 and imaging conditions are correlated may be stored in the memory unit 55, corresponding to the identifying information of the radiation detector 30. Thereby, imaging conditions can be set according to the identifying information of the radiation detector 30 obtained from the photographed image G1, by referring to the table. In addition, in the case that imaging conditions for a previous occasion in which the same radiation irradiating apparatus 10 and the same radiation detector 30 were employed to image the same subject H are stored, imaging conditions may be set taking the imaging conditions of the previous imaging operation into consideration.

Figure 13:
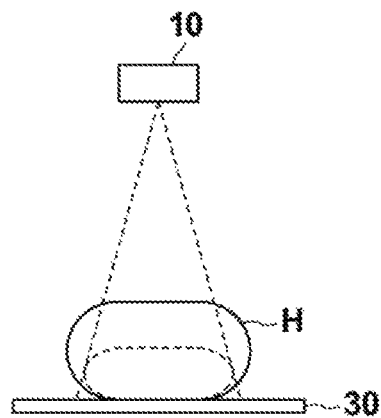
FIG. 13 is a diagram that illustrates changes in an irradiation field according to the body thicknesses of subjects.

Here, the size of the irradiation field of radiation irradiated from the radiation irradiating apparatus 10 differs for a case in which the body thickness of the subject H is large and a case in which the body thickness of the subject H is small, as illustrated in FIG. 13. Specifically, the size of the irradiation field is greater for smaller body thicknesses. For this reason, the control unit 59 calculates the body thickness of the subject H from the SID and SOD. Further, the control unit 59 obtains information regarding the irradiation field, constituted by information regarding the center position and the size of an irradiation field region, based on information regarding the range regulated by the collimator 14, which is transmitted from the radiation irradiating apparatus 10. Then, the control unit 59 transmits detector information, information related to the detector, information related to the irradiation field, and imaging conditions to the radiation irradiating apparatus 10 (Information Transmission: step ST8). Note that the identifying information is transmitted in the case that the obtained identifying information is that of a radiation detector that should be utilized, as described above.

The drive control unit 23 of the radiation irradiating apparatus 10 displays the identifying information of the radiation detector 30, the drive state of the radiation detector 30, the vertical direction of the radiation detector 30, the remaining battery power of the battery of the radiation detector 30, the region corresponding to the radiation detector 30, the center position of the radiation detector 30, and the irradiation field of radiation which is regulated by the collimator 14, on the monitor 15 overlapped on the photographed image G1, based on the information transmitted from the console 50 (Information Display: step ST9).

Figure 14:
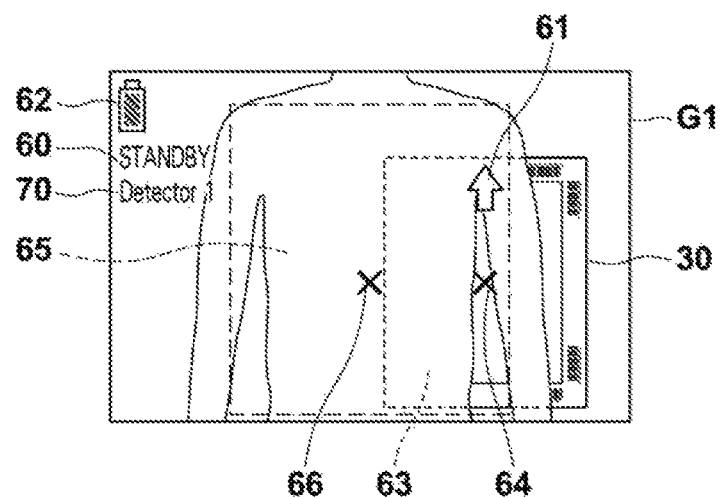
FIG. 14 is a diagram that illustrates a photographed image onto which various pieces of information are overlapped.

FIG. 14 is a diagram that illustrates a photographed image onto which various pieces of information are overlapped. As illustrated in FIG. 14, text 60 that represents the drive state of the radiation detector 30 (here, "STANDBY"), an arrow 61 that represents the vertical direction of the radiation detector 30, an icon 62 that represents the remaining battery power of the radiation detector 30, a detection region 63 corresponding to the detection region of the radiation detector 30, the center position 64 of the radiation detector 30, the irradiation field region 65, the center position 66 of the irradiation field region 65, and text 70 reading "Detector 1", which is the identifying information of the radiation detector 30, are overlapped on a photographed image G1 which is being displayed on the monitor 15. Note that the center position 66 of the irradiation field region 65 is also displayed within the irradiation field region 65. Note that it is preferable for the detection region 63 and the irradiation field region 65 to be displayed such that they can be discriminated from each other. It is preferable for the detection region 63 and the irradiation field region 65 to be displayed in different colors, for example. The colors may be specified according to commands from the console 50.

In the present embodiment, markers are provided at the four corners of the radiation detector 30. Therefore, at least one of the markers is included in the photographed image G1, even if a portion of the radiation detector 30 is hidden by the subject H, as illustrated in FIG. 14.

In addition, it is preferable for the control unit 59 to detect the color of clothing worn by the subject H from the photographed image G1, and to specify the colors of the detection region 63 and the irradiation field region 65 such that these colors are different from the color of the clothing worn by the subject H, in the console 50. Thereby, it will become possible to prevent the detection region 63 and the irradiation field region 65 which are overlapped onto the photographed image G1 from being confused with the clothing worn by the subject H.

Then, the camera 13 of the radiation irradiating apparatus 10 continues to photograph the subject H to obtain photographed images G1 of the subject H, and the radiation irradiating apparatus 10 transmits the photographed images G1 to the console 50 (Photographed Image Transmission: step ST10). Note that the radiation detector 30 continues to transmit information that represents the drive state of the radiation detector 30, information that represents the remaining battery power of the battery of the radiation detector 30, movement information detected by the motion sensor 36, etc.

The control unit 59 of the console 50 judges whether the radiation detector 30 is included in the photographed image G1, by judging whether any one of the markers 34A through 34D is included in the photographed image G1 (step ST11). In the case that the result of judgment at step ST11 is affirmative, the control unit 59 transmits radiation detector position information that represents the position of the radiation detector 30 within the photographed image G1, based on any one of the markers 34A through 34D provided on the radiation detector 30 which is included in the photographed image G1 (step ST12). The drive control unit 23 of the radiation irradiating apparatus 10 displays the detection region 63 of the radiation detector 30 overlapped on the photographed image G1, based on the radiation detector position information transmitted from the console (Display Information: step ST13).

Meanwhile, there are cases in which the radiation detector 30 moves to a position outside the angle of view of the camera 13 and is no longer included in the photographed image G1, if the radiation detector 30 is moved after it is included in the photographed image G1. In addition, if the radiation detector 30 is completely obscured by the subject H, the radiation detector 30 will not be included in the photographed image G1. In such cases, the markers 34A through 34D will not be included in the photographed image G1, and therefore the position of the radiation detector 30 cannot be specified only from the photographed image G1. In this case, the result of judgment in step ST11 will be negative. In the case that the result of judgment in step ST11 is negative, the control unit 59 of the console 50 obtains radiation detector position information based on movement information which is detected by the motion sensor 38 and transmitted from the radiation detector 30, and transmits the obtained radiation detector position information to the radiation irradiating apparatus 10 (step ST14).

Figure 15:
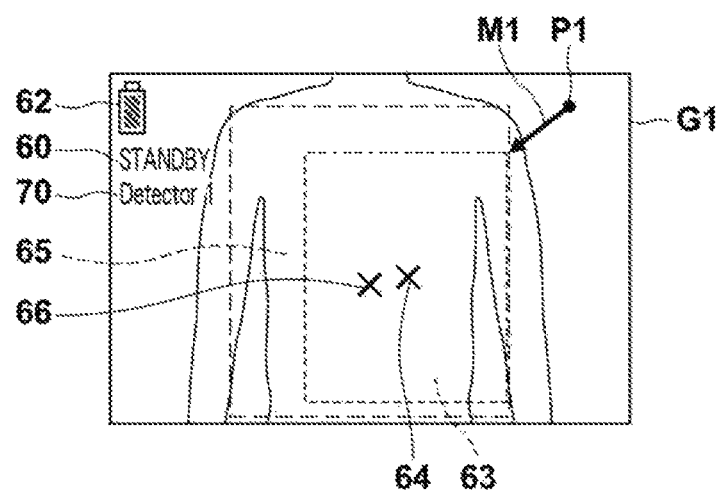
FIG. 15 is a diagram for explaining obtainment of radiation detector position information based on movement information.

FIG. 15 is a diagram for explaining obtainment of radiation detector position information based on movement information. In FIG. 15, the position of any one of the markers 34A through 34D on the radiation detector 30 at a point in time when any one of the markers 34A through 34D was included in the photographed image G1 is set as a reference position P1. Then, the movement information and the size of the detection region of the radiation detector 30 are employed to calculate an amount of movement M1 of the radiation detector 30 from the reference position P1. Then, the radiation detector position information is obtained based on the calculated amount of movement M1. Thereby, the position of the radiation detector 30 can be tracked, even if the radiation detector 30 is no longer included in the photographed image G1. Accordingly, the detection region 63 and the center position 64 of the radiation detector 30 can be overlapped and displayed on the photographed image G1, as illustrated in FIG. 15.

Figure 16:
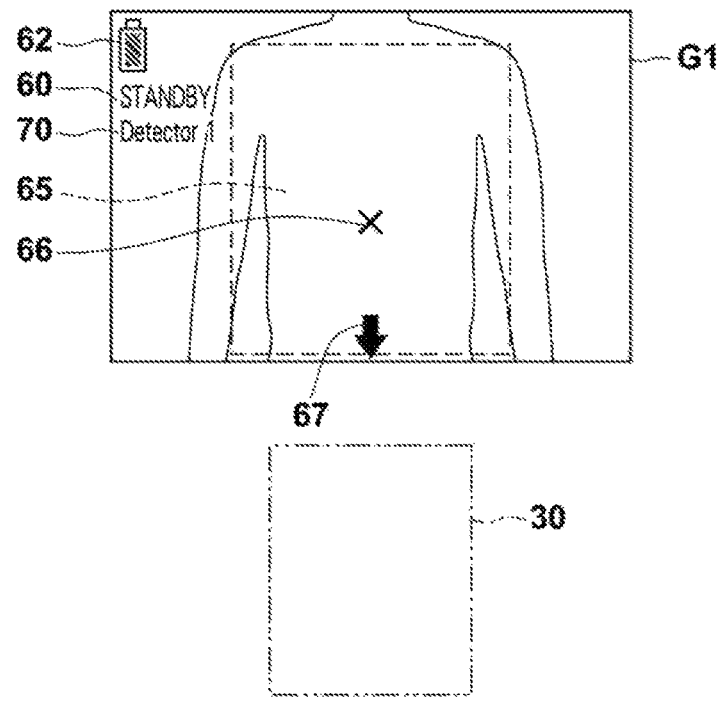
FIG. 16 is a diagram that illustrates a photographed image onto which information that represents the direction in which a radiation detector is present is overlapped.

Note that information that represents the direction in which the radiation detector 30 is present may be displayed on the photographed image G1, employing the radiation detector position information which is obtained based on the movement information of the radiation detector 30, in the case that it is judged that the photographed image G1 does not include any one of the markers 34A through 34D after it is judged that the photographed image G1 includes any one of the markers 34A through 34D, that is, in the case that the radiation detector 30 is no longer included in the photographed image G1 after the radiation detector 30 was included in the photographed image G1. FIG. 16 is a diagram that illustrates a photographed image G1 onto which information that represents the direction in which the radiation detector 30 is present is overlapped, along with various other types of information. In FIG. 16, the position at which the radiation detector 30 is present is indicated by dotted lines. As illustrated in FIG. 16, an arrow 67 is displayed on the monitor 15 as information that represents the direction in which the radiation detector 30 is present, in addition to the information which is overlapped on the photographed image G1 illustrated in FIG. 14. Note that text reading "UP", "DOWN", "LEFT", or "RIGHT" may be the information that represents the direction in which the radiation detector 30 is present, instead of the arrow 67.

The operators of the radiation irradiating apparatus 10 and the radiation detector 30 cooperate to perform the operations prior to imaging. That is, the operator of the radiation detector 30 moves the radiation detector 30 to an appropriate position behind the subject H, and the operator of the radiation irradiating apparatus 10 confirms whether the radiation detector 30 has been moved to an appropriate position while viewing the image which is being displayed on the monitor 15. In addition, the operator of the radiation irradiating apparatus 10 moves the radiation irradiating apparatus 10 if necessary. By these operations, the center position 66 of the irradiation field region 65 and the center position 64 of the detection region 63 can be aligned.

Figure 17:
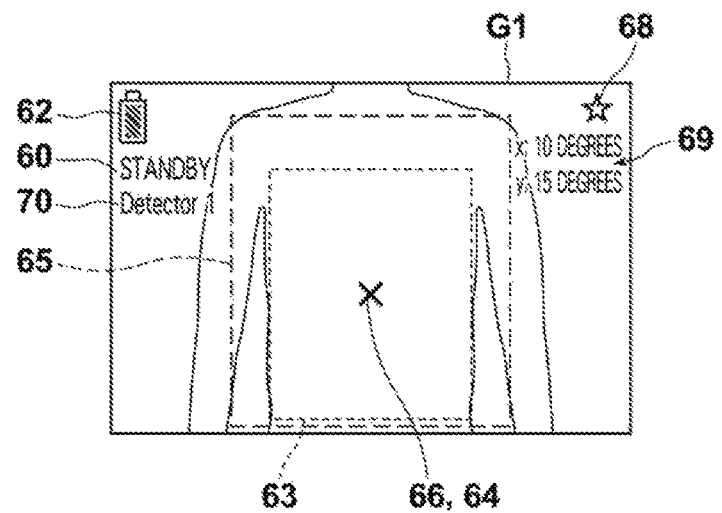
FIG. 17 is a diagram that illustrates a state in which the center position of an irradiation field region and the center position of a detection region are aligned.

In addition, the control unit 59 may judge whether the center position 66 of the irradiation field region 65 and the center position 64 of the detection region 63 are aligned, and information that represents that the center positions are aligned may be transmitted to the radiation irradiating apparatus 10, in the case that the center positions are aligned. In the case that the radiation irradiating apparatus 10 receives the information that represents that the center positions are aligned, text that reads "The center positions are aligned", a mark that indicates that the center positions are aligned, etc., is displayed on the monitor 15, for example. FIG. 17 illustrates a star shaped mark 68 that indicates that the center positions are aligned. Note that any alternative technique, such as audio output and causing the monitor 15 to blink, may be employed, as long as it is capable of notifying the operator that the center positions are aligned.

In addition, in the case that the center position 66 of the irradiation field region 65 and the center position 64 of the detection region 63 are aligned, information regarding the inclination of the radiation detector 30 may be overlapped and displayed on the photographed image G1, based on the information regarding the inclination of the radiation detector 30 which is included in the movement information of the radiation detector 30. Here, the inclination of the radiation detector 30 with respect to the radiation irradiating apparatus 10 is a two dimensional inclination with a plane that perpendicularly intersects with the radiation irradiation axis as a reference. Note that in the case that an x axis and a y axis are set on the plane of the radiation detector 30, the inclination is the angle of inclination about each of the x axis and the y axis. The control unit 59 of the console 50 obtains information regarding the inclination of the radiation detector and transmits the information to the radiation irradiating apparatus 10 in the case that the center position 66 of the irradiation field region 65 and the center position 64 of the detection region 63 are aligned. The radiation irradiating apparatus 10 displays the angles of inclination about the x axis and the y axis on the monitor 15 in the case that the information regarding the inclination of the radiation detector 30 is received. FIG. 17 illustrates a state in which angle information 69 that represents angles about the x axis and the y axis is displayed. Thereby, the operator can adjust the inclination of the radiation detector 30 such that the angles about the x axis and the y axis are zero, resulting in the radiation irradiation axis and the radiation detector 30 intersecting perpendicularly.

Note that the control unit 59 may employ the movement information of the radiation irradiating apparatus 10 to calculate the relative inclination between the radiation irradiating apparatus 10 and the radiation detector 30, and transmit the calculated relative inclination to the radiation irradiating apparatus 10. In this case, the relative inclination of the radiation detector 30 with respect to the radiation irradiating apparatus 10 can be adjusted by adjusting the inclination of the radiation irradiating apparatus 10 after fixing the radiation detector 30. Note that the color of the detection region 63 which is overlapped onto the photographed image G1 may be changed, or the detection region may be caused to blink, in the case that the radiation irradiation axis and the radiation detector 30 become perpendicular to each other. Thereby, the operator can easily recognize that the radiation irradiation axis and the radiation detector 30 have become perpendicular to each other.

Here, in the state illustrated in FIG. 17, the irradiation field region 65 is larger than the detection region 63. Therefore, radiation which is not irradiated onto the radiation detector 30 among the radiation which has passed through the subject H cannot be utilized to form an image, and will become wasted. In addition, irradiating such wasted radiation onto the subject H will result in the radiation dosage received by the subject H becoming great.

Figure 18:
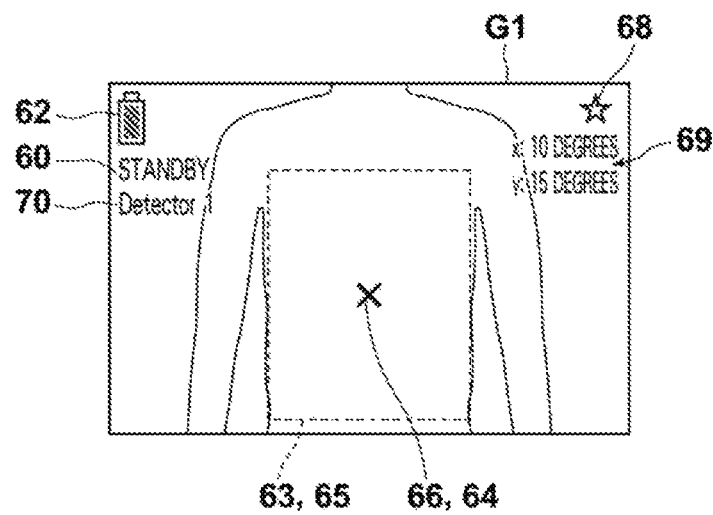
FIG. 18 is a diagram that illustrates a state in which an irradiation field region and a detection region are aligned.
Figure 19:
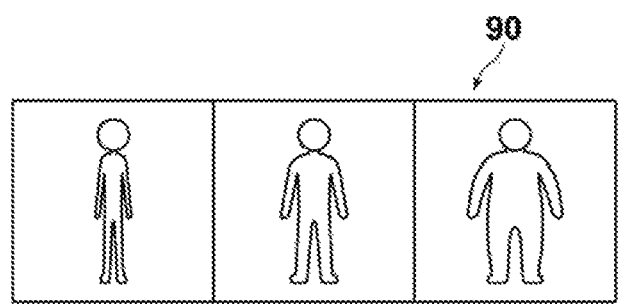
FIG. 19 is a diagram that illustrates icons of a thin person, a normal person, an obese person, etc.

For these regions, the operator of the radiation irradiating apparatus 10 employs the input unit 24 to cause the irradiation field region 65 and the detection region 63 to match. For this reason, the drive control unit 23 of the radiation irradiating apparatus 10 judges whether a region matching command has been input (step ST15). Note that the region matching command is a command is a command which is input by the operator manipulating the irradiation field region 65 displayed on the monitor 15 with a finger or the like, to cause the irradiation field region 65 and the detection region 63 to match, as illustrated in FIG. 18.

In the case that the result of judgment at step ST15 is negative, the process returns to step ST10. Thereby, the photographed image G1 continues to be transmitted to the console 50, and the console 50 continues to obtain radiation detector position information. Note that if movement of the radiation detector 30 is continued, there are cases in which it is judged that any one of the markers 34A through 34D, that is, the radiation detector 30, is included in the photographed image G1 after it has been judged that any one of the markers 34A through 34D, that is, the radiation detector 30, is not included in the photographed image G1. In such cases, the judgment at step ST11 becomes affirmative, and radiation detector position information is obtained based on any one of the markers 34A through 34D of the radiation detector 30 which is included in the photographed image G1.

Here, the collimator 14 may be driven by the collimator control unit 21 coordinated with the region matching command. However, if the collimator 14 is driven each time that a command to match the irradiation field region 65 and the detection region 63 is input, the amount of power consumption will become great. For this reason, the collimator 14 may be driven by the collimator control unit 21 after the command to match the irradiation field region 65 and the detection region 63 is input through the input unit 24, and input indicating that preparations for imaging have been completed is received by the input unit 24, in the present embodiment.

Further, in the case that the result of judgment at step ST15 is affirmative, the drive control unit 23 of the radiation irradiating apparatus 10 judges whether preparations for imaging have been completed (step ST16). Whether preparations for imaging have been completed may be determined by receiving input from the input unit 24 as described above. In the case that the result of judgment at step ST16 is negative, the process returns to step ST10.

In the case that the result of judgment at step ST16 is affirmative, the drive control unit 23 turns the irradiation field lamp 29 ON, and drives the collimator 14 using the collimator control unit 21, to set an irradiation field (step ST17). At this time, it is preferable for the irradiation field region 65 which is being displayed on the monitor 15 to blink or the like, to notify the operator that the collimator 14 is being driven. Note that the drive control unit 23 of the radiation irradiating apparatus 10 does not enable operations of the imaging button 18 to be received while the collimator 14 is being driven. When the driving of the collimator 14 is complete, the drive control unit 23 detects movement of the radiation irradiating apparatus 10 using the motion sensor 28, and calculates the amount of movement of the radiation irradiating apparatus 10 per unit time (step ST18). The amount of movement of the radiation irradiating apparatus 10 per unit time corresponds to the amount of shaking of the operator's hands. The drive control unit 23 judges whether the amount of movement per unit time is less than a threshold value Th1 (step ST19). In the case that the result of judgment at step ST19 is negative, the drive control unit 23 displays a warning on the monitor 15 (step ST20), and the process returns to step ST18. The operator may hold the radiation irradiating apparatus 10 more steadily or the like, in response to the displayed warning.

Note that in the case that the result of judgment at step ST19 is negative, the drive control unit 23 controls the radiation source 19 such that radiation is not emitted even if the imaging button 18 is operated. As an alternative, the drive control unit 23 may prevent operation of the imaging button 18 by locking the imaging button 18 or the like. In addition, the threshold value Th1 may be changed according to the irradiation time, which is included in the imaging conditions. For example, the influence of the amount of shaking of the operator's hands will become greater as the irradiation time of radiation is longer. Therefore, the threshold value Th1 may be set lower as the irradiation time of radiation becomes longer.

In the case that the result of judgment at step ST19 is affirmative, the drive control unit 23 judges whether an imaging command has been input through the input unit 24 (step ST21). In the case that the result of judgment at step ST21 is negative, the process returns to step ST18. In the case that the result of judgment at step ST21 is affirmative, the drive control unit 23 drive the radiation source 19 to emit radiation toward the subject H, thereby irradiating radiation onto the subject H (step ST22). Note that in the case that the result of judgment at step ST19 is affirmative, the drive control unit 23 may display a message indicating the imaging is possible on the monitor 15. Note that in the case that the result of judgment at step ST19 becomes affirmative after being negative, the drive control unit 23 ceases display of the warning on the monitor 15, and enables the radiation source 19 to be driven by operation of the imaging button 18. In addition, in the case that operation of the imaging button 18 had been precluded, the locking of the imaging button 18 is released, in order to cause the imaging button 18 to become operable.

The radiation detector 30 detects radiation which has passed through the subject H to obtain a radiation image G2 of the subject H (step ST23). The obtained radiation image G2 is transmitted to the console 50. The image processing unit 52 administers image processes on the radiation image G2 to improve the image quality thereof. The processed radiation image G2 is output to the output unit 54. In addition, the control unit 59 transmits the processed radiation image G2 to the radiation irradiating apparatus 10 (step ST24).

The drive control unit 23 of the radiation irradiating apparatus 10 displays the radiation image G2 on the monitor 15 (step ST25), and the process is completed. In this case, the photographed image G1 and the radiation image G2 may be displayed in an overlapped manner, or only the radiation image G2 may be displayed. Thereby, whether the radiation image G2 has been obtained appropriately can be determined.

As described above, the present embodiment detects any one of the markers 34A through 34D of the radiation detector 30 from the photographed image G1, and obtains identifying information of the radiation detector 30 from the markers 34A through 34D in the case that any one of the markers 34A through 34D is detected. Therefore, the identifying information of the radiation detector can be input into the console 50 only by photographing the radiation detector 30 with the camera 13. Accordingly, the burden of operations to input identifying information of the radiation detector 30 into the console 50 on an operator can be reduced.

Note that in the embodiment described above, each of a plurality of markers is provided in the vicinities of different corners of the radiation detector 30. Alternatively, each of a plurality of markers may be provided in the vicinities of different edges of the radiation detector 30. As a further alternative, each of a plurality of markers may be provided in the vicinities of different corners and in the vicinities of different edges of the radiation detector 30.

In the embodiment described above, linear bar codes were employed as the markers 34A through 34D. Alternatively, two dimensional bar codes may be employed as the markers 34A through 34D.

In the embodiment described above, the control unit 59 of the console 50 performs the process of obtaining the identifying information of the radiation detector 30 and the process of identifying the radiation detector 30 based on the identifying information. Alternatively, these processes may be performed by the radiation irradiating apparatus 10. In this case, the drive control unit 23 may perform these processes, or a dedicated means for performing these processes may be provided in the radiation irradiating apparatus 10.

In addition, in the embodiment described above, the distance sensor 27 detects SID and SOD, and the body thickness of the subject H is calculated from the SID and SOD. Alternatively, an operator may input the body thickness of the subject H using the input unit 24 of the radiation irradiating apparatus 10. In this case, a body thickness which is measured may be input. Alternatively, icons 90 that represent a thin person, a person with a normal body shape, and a fat person may be displayed on the monitor 15, and input of the body thickness may be performed by the operator selecting one of the displayed icons 90.

In addition, the radiation irradiating apparatus 10 of the present embodiment is portable. Therefore, it may be possible to emit radiation toward directions in which the subject H is not present. It is preferable for the drive control unit 23 to control the radiation source 19 such that radiation cannot be emitted in states in which the photographed image G1 does not include objects necessary for imaging, such as the radiation detector 30, in order to prevent such emissions.

In addition, SID and SOD are measured by the distance sensor 27 before initiating operations prior to imaging in the embodiment described above. Alternatively, SID and SOD may be measured by the distance sensor 27 during the operations prior to imaging. Further, in this case, the positions at which SID and SOD are to be measured may be specified on the monitor 15, and information regarding the specified positions may be transmitted to the console 50. Thereby, it will become possible to identify the positions of the subject H at which the body thickness is being measured at the console 50.

In addition, the control unit 59 of the console 50 sets the imaging conditions in the embodiment described above. Whether irradiation of radiation at the set imaging conditions is possible may be judged based on the information regarding the remaining power in the battery 26 of the radiation irradiating apparatus 10. In the case that it is judged that irradiation of radiation at the set imaging conditions is not possible, information indicating the result of judgment may be transmitted to the radiation irradiating apparatus 10. The operator can recognize that the remaining power of the battery 26 is insufficient, by the monitor 15 of the radiation irradiating apparatus 10 displaying the information indicating that imaging cannot be performed. Accordingly, the operator may take measures such as exchanging the battery, preparing another radiation irradiating apparatus 10, or the like.

In the embodiment described above, the console 50 may transmit the photographed image G1, the identifying information of the radiation detector 30, the radiation detector position information, the information representing the vertical direction, the center position information, the information that represents the drive state of the radiation detector 30, and the information regarding the remaining battery power to the terminal 80. The various pieces of information may be overlapped and displayed on the photographed image G1 at the terminal 80 in the same manner as the display on the monitor 15. Thereby, a physician or the like can monitor the state of the operations prior to imaging of the subject H at their own terminal 80.

In the embodiment described above, there may be cases in which the vertical direction of the radiation detector 30 is the horizontal direction of the photographed image G1. In addition, there may be cases in which the top and bottom of the radiation detector 30 are opposite the top and bottom of the photographed image G1. In such cases, the top and bottom of an obtained radiation image G2 will not match the top and bottom of the photographed image G1. Therefore, if the obtained radiation image G2 is displayed as is, the radiation image G2 will be difficult to view. In the present embodiment, the vertical direction of the radiation detector 30 is detected at the console 50. Therefore, the radiation image G2 may be rotated such that the top and bottom of the displayed radiation image G2 will be correct. By rotating the radiation image G2 such that the top and bottom thereof will be correct, the top and bottom of the photographed image G1 and the top and bottom of the radiation image G2 can be matched. As a result, viewing of the displayed radiation image G2 is facilitated.

In the embodiment described above, there may be cases in which the amount of movement of the radiation irradiating apparatus 10 per unit time will become greater than or equal to the threshold value Th1 while radiation is being irradiated. In such cases, emission of radiation may be temporarily ceased, and radiation may be emitted again for the remaining radiation irradiation time after the amount of movement of the radiation irradiating apparatus 10 per unit time becomes less than the threshold value Th1. In this case, two radiation images will be obtained prior to and following the cessation of emission of radiation. However, the console 50 may combine the two radiation images by addition or the like to generate an ultimate radiation image G2.

In the embodiment described above, the irradiation field lamp 29 is turned ON when preparations for imaging are completed. Alternatively, the irradiation field lamp 29 may be switched ON or OFF. For example, in the case that a radiation image G2 of the face of an animal is to be obtained, it is necessary to irradiate radiation onto the face of the animal. In such a case, if the irradiation field lamp 29 is turned ON, light will be irradiated onto the face of the animal, and there is a possibility that the animal will become startled. For this reason, the control unit 59 of the console 50 may judge the portion of the subject H included in the photographed image G1 to be imaged, and to cause the irradiation field lamp 29 to not be turned ON even when the command that preparations for imaging have been completed is input in the case that the portion is the face of an animal. Thereby, the animal can be prevented from becoming startled by the visible light which is emitted from the irradiation field lamp 29. Note that the operator will be aware of the portion of the subject H to be imaged. Therefore, whether the irradiation field lamp 29 is to be turned ON or OFF may be switched by a command input by the operator through the input unit 24.

In the embodiment described above, the amount of movement of the radiation irradiating apparatus 10 per unit time is calculated employing the amount of movement detected by the motion sensor 28. Here, in the present embodiment, the photographed image G1 is obtained at a frame rate which is determined in advance. Therefore, the amount of movement of the radiation irradiating apparatus 10 per unit time may alternatively be calculated based on two photographed images obtained at different photography timings and the difference in photography times of the two photographed images.

In the embodiment described above, the detection region 63 corresponding to the detection region of the radiation detector 30 is overlapped onto the photographed image G1, to display the region corresponding to the radiation detector on the photographed image G1 such that it can be discriminated. Alternatively, a region surrounded by the four side surfaces 32C, 32D, 32E, and 32F of the chassis 32 of the radiation detector 30 may be overlapped on the photographed image G1, to display the region corresponding to the radiation detector on the photographed image G1 such that it can be discriminated.

In the embodiment described above, the camera 13 may be an infrared camera that employs infrared rays and is capable of measuring the temperature distribution within the photography range thereof, and infrared images that represent the temperature distributions within the photography range may be employed as the photographed image G1. In this case, the photographed image G1 obtained by the camera 13 is that which represents the temperature distributions of the surface of the subject H and objects in the periphery thereof. By employing a camera 13 capable of obtaining infrared images as the photographed image G1, the position of a subject H can be specified within the photographed image G1 by the temperature distribution represented in the photographed image G1, even in cases that the subject H is covered by a sheet or the like at the site of a natural disaster.

In the case that such an infrared camera is employed, it is preferable for the marker to be formed by a material that reflects infrared rays. For example, in the case that the marker is a bar code, the marker may be formed by printing the bar code using a material that absorbs infrared rays onto a material that reflects infrared rays. Alternatively, if a light emitting device such as an LED is employed as the marker, a light emitting device that emits infrared rays may be employed.

Note that it is preferable for the camera 13 to be that which is capable of switching between photography using visible light and photography using infrared rays. In the case that the camera 13 which is employed is capable of switching between photography using visible light and photography using infrared rays, first, the subject H is photographed using infrared rays to obtain a photographed image G1 that represents a temperature distribution. The photographed image G1 that represents the temperature distribution is employed to determine the position of the irradiation field first. Thereafter, the camera 13 is switched to perform photography using visible light, and the detection region of the radiation detector 30 and the irradiation field region are overlapped and displayed on the photographed image G1 in the same manner as in the embodiment described above. Thereafter, the photographed image G1 may be employed to align the position of the radiation detector 30 such that the detection region of the radiation detector 30 and the irradiation field region match. Thereby, a radiation image G2 can be obtained by matching the region of the radiation detector 30 and the irradiation field region even in a case in which the subject H is covered by a sheet or the like.

Note that by displaying the photographed image G1, which is an infrared image, on the monitor 15 in this manner, abnormalities in the body temperature of the subject H such as heatstroke and accidental hypothermia. In addition, the radiation image G2 obtained by imaging and the photographed image G1, which is an infrared image, may be arrayed and displayed on the monitor 15. Thereby, the infrared image and the radiation image G2 can be compared. Particularly in the case that treatment of an abnormality in body temperature is performed prior to radiation imaging, the course of treatment can be confirmed by continuously displaying the infrared image.

Figure 20:
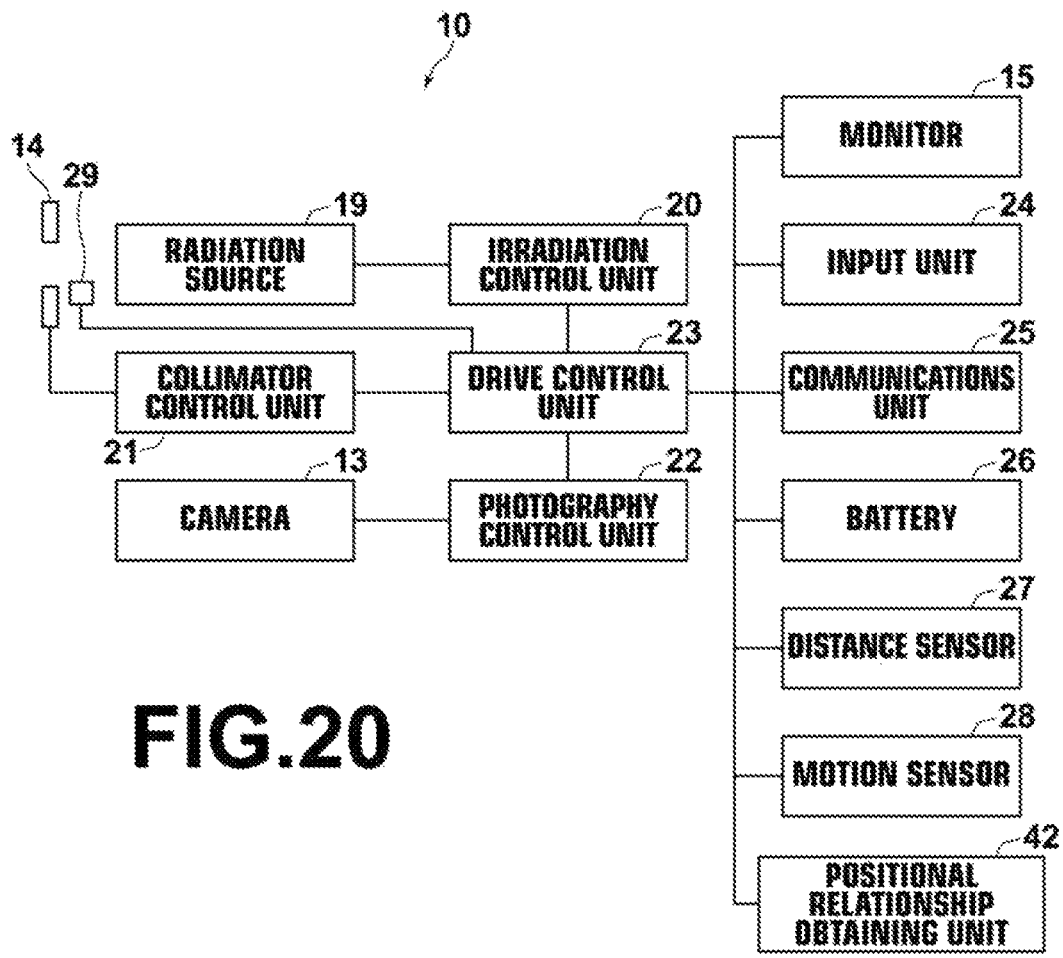
FIG. 20 is a schematic block diagram that illustrates the inner components of another example of a radiation irradiating apparatus.

In the embodiment described above, the relative positional relationship between the radiation detector 30 and the camera 13 may be obtained based on at least one of the size and shape of any one of the markers 34A through 34D which is detected within the photographed image G1. In this case, the radiation irradiating apparatus 10 is further equipped with a positional relationship obtaining unit 42 that obtains the relative positional relationship between the radiation detector 30 and the camera 13 based on at least one of the size and shape of any one of the markers 34A through 34D which is detected within the photographed image G1, as illustrated in FIG. 20. Note that here, the distance between the radiation detector 30 and the camera 13, that is, the radiation irradiating apparatus 10, and the inclination of the radiation irradiation axis of the radiation irradiating apparatus 10 with respect to an axis perpendicular to the detecting surface of the radiation detector 30 are obtained as a positional relationship, employing both of the size and shape of any one of the markers 34A through 34D which is detected within the photographed image G1.

Here, the size of the markers 34A through 34D included in the photographed image G1 will become larger as the distance between the radiation detector 30 and the camera 13 is smaller. For this reason, the positional relationship obtaining unit 42 detects the markers 34A through 34D from within the photographed image G1, and calculates the relative distance between the radiation detector 30 and the camera 13 from the size of the detected markers. Specifically, the size of a marker which is photographed as a distance which is determined in advance is designated as a standard, and the relative distance between the radiation detector 30 and the camera 13 is calculated based on the difference in the size of a marker which is detected within the photographed image G1 and the standard size.

Figure 21:
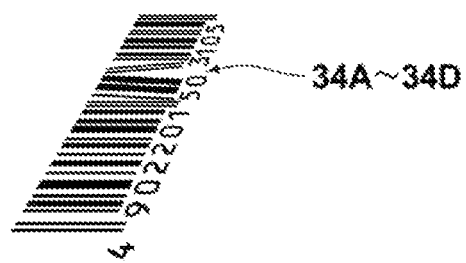
FIG. 21 is a diagram that illustrates a marker having a distorted shape.

Meanwhile, if the radiation irradiation axis of the radiation irradiating apparatus 10 is inclined with respect to the axis perpendicular to the detecting surface of the radiation detector 30, the shape of the bar code markers 34A through 34D which are included in the photographed image G1 will become distorted, as illustrated in FIG. 21. For this reason, the positional relationship obtaining unit 42 detects the markers 34A through 34D from within the photographed image G1, and calculates the inclination of the radiation irradiation axis of the radiation irradiating apparatus 10 with respect to the axis perpendicular to the detecting surface of the radiation detector 30 based on the distortion in the shape of the detected markers. Specifically, the shape of a marker which is photographed in a state in which the radiation irradiation axis is perpendicular to the radiation detector 30 is designated as a standard, and the inclination of the radiation irradiation axis of the radiation irradiating apparatus 10 with respect to the axis perpendicular to the detecting surface of the radiation detector 30 is calculated based on the distortion in the shapes of markers which are detected within the photographed image with respect to the standard shape. Note that at this time, it is preferable for the detected markers to be enlarged.

The obtained positional relationship is displayed on the monitor 15. The operator may view the positional relationship displayed on the monitor 15, and change the distance between the radiation detector 30 and the radiation irradiating apparatus 10. In addition, the operator may adjust the inclination of the radiation irradiation axis of the radiation irradiating apparatus 10 with respect to an axis perpendicular to the detecting surface of the radiation detector 30.

Note that a warning may be issued in the case that the distance included in the obtained positional relationship is greater than a predetermined threshold value, or in the case that the inclination between the two axes is greater than a predetermined threshold value. Specifically, text that indicates that the distance included in the obtained positional relationship is greater than a predetermined threshold value, or that the inclination between the two axes is greater than a predetermined threshold value may be displayed on the monitor 15.

Figure 22:
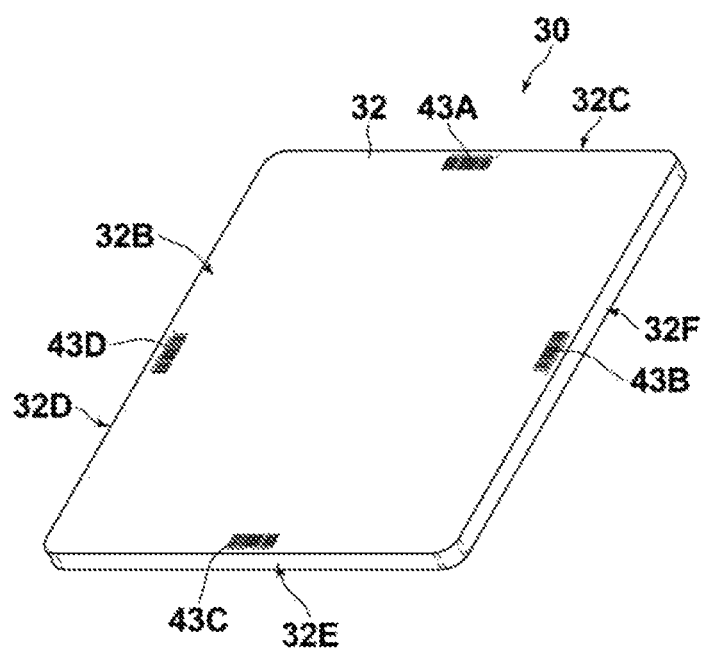
FIG. 22 is a perspective view of a radiation detector as viewed from the rear.

In the embodiment described above, the rear surface 32B of the radiation detector 30 may be provided with a marker that represents that the surface is the rear surface. FIG. 22 is a perspective view of a radiation detector as viewed from the rear. As illustrated in FIG. 22, markers 43A through 43D, which are different from the markers 34A through 34D, are provided on the rear surface 32B of the chassis 32 of the radiation detector 30 in the vicinities of the four side surfaces 32C, 32D, 32E, and 32F. The markers 43A through 43D include information representing that they are provided on the rear surface 32B of the radiation detector 30. Note that in FIG. 22, the markers 43A through 43D are linear bar codes. However, the markers 43A through 43D may be symbols which are not included on the front surface 32A, simple line segments, or colors, as long as it can be understood that they are provided on the rear surface 32B. In addition, the markers 43A through 43D may be light emitting elements that represent that they are provided on the rear surface 32B. In the case that light emitting elements are employed, the arrangement of the light emitting elements may be different between the front surface 32A and the rear surface 32B, or the color of emitted light may be different between the front surface 32A and the rear surface 32B.

In the case that the markers are detected within the photographed image G1, in the case that the detected markers are any one of the markers 43A through 43D, it will be understood that the radiation detector 30 is provided with the rear surface 32B thereof facing the radiation irradiating apparatus 10. Accordingly, if an indication is displayed on the monitor 15 in such a case, the operator can recognize the erroneous orientation of the radiation detector 30, and can reposition the radiation detector 30 such that the front surface 32A thereof faces the radiation irradiating apparatus 10.

In the case that light emitting elements are employed as markers in the embodiment described above, the detector information of the radiation detector 30 may be represented by at least one of the lighting pattern of the light, the blinking pattern of the light, and the color of the light emitted by the light emitting elements. Here, the detector information includes information that represents the drive state of the radiation detector 30, information that represents the remaining battery power of the radiation detector 30, movement information detected by the motion sensor 38, etc., as described above. The radiation irradiating apparatus 10 is capable of exerting various types of control according to at least one of the lighting pattern of the light, the blinking pattern of the light, and the color of the light emitted by the light emitting elements detected within the photographed image G1.

For example, in the case that the color of the light emitted by the light emitting elements represents the drive state of the radiation detector 30, the drive state of the radiation detector 30 can be identified by detecting the color of the light emitted by the light emitting elements. Here, in the case that the drive state of the radiation detector 30 is "Power ON", commands may be issued from the radiation irradiating apparatus 10 to the radiation detector 30 to change the drive state of the radiation detector 30 according to the drive state of the radiation irradiating apparatus 10. For example, in the case that the drive state of the radiation detector 30 is "Power ON", and the result of step ST19 illustrated in FIG. 12 is affirmative, a command to change the drive state of the radiation detector 30 to a "READY" state, in which preparations for detecting a radiation image have been completed, may be issued from the radiation irradiating apparatus 10 to the radiation detector 30. Thereby, the drive state of the radiation detector 30 can be changed to a ready state, in which imaging operations are capable of being performed immediately.

Figure 23:
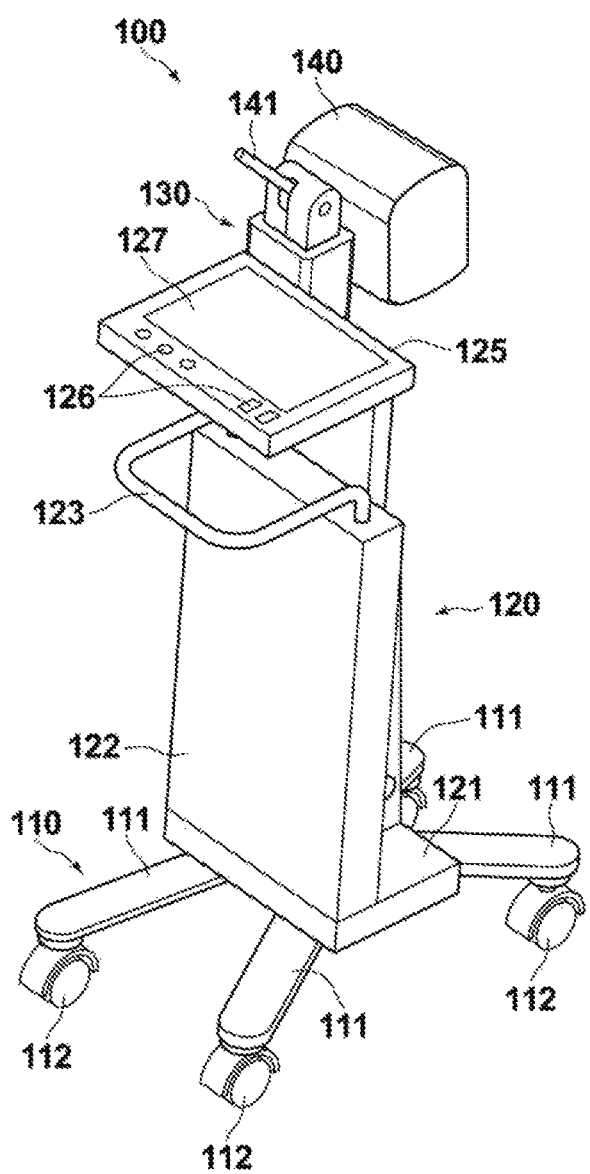
FIG. 23 is a perspective view that illustrates the entirety of a radiation irradiating apparatus configured to be capable of movement.

In addition, the portable radiation irradiating apparatus 10 is utilized in the embodiment described above. Alternatively, a radiation irradiating apparatus which is configured to be movable, in order to prevent shaking of the operator's hands and irradiation of radiation onto the operator's hands, as well as to enable movement in cluttered locations such as emergency sites and intensive care units, may be employed. FIG. 23 is a perspective view that illustrates the entirety of a radiation irradiating apparatus configured to be capable of movement. FIG. 24 is a side view that illustrates the radiation irradiating apparatus configured to be capable of movement in a state of use. The radiation irradiating apparatus 100 which is configured to be capable of movement has leg portions 110 which are configured to be capable of movement on a surface on which the apparatus is placed, a main body portion 120 held above the leg portions 110, an arm portion 130 linked to the main body portion 120, and a radiation source portion 130 mounted on the distal end of the arm portion 130.

The leg portions 110 have four legs 111 and wheel portions 112 which are mounted on the lower surfaces of the distal ends of each of the legs 111. Note that braking means (not shown) are provided on the wheel portions 112.

The main body portion 120 houses an irradiation control unit 20, a collimator control unit 21, a photography control unit 22, a drive control unit 23, a communications unit 25, and a battery 26 within a chassis 122 fixed on a base portion 121, in a manner similar to that of the radiation irradiating apparatus 10 of the embodiment described above. A handle 123 for pushing and pulling the radiation irradiating apparatus 100 is provided on the upper end of the chassis 122. In addition, an operating unit 125 is provided on the upper portion of the base portion 121.

The operating unit 125 is equipped with an input unit 126 constituted by operating buttons, switches, etc. for inputting signals to command various operations of the radiation irradiating apparatus 100, a monitor 127 for displaying various types of information, etc. Note that the input unit 126 may be constituted by a touch panel in the same manner as in the radiation irradiating apparatus 10 of the embodiment described above.

The arm portion 130 is constituted by a plurality of members 131, 132, and 133 that form a nested structure. The member 132 and the member 133 are connected by a rotatable holding mechanism, and the member 133 is configured to rotate in a direction that changes the angle thereof with respect to the member 132.

The radiation source portion 140 is mounted on the distal end of the member 133 of the arm portion 130 so as to swing freely therefrom. The radiation source portion 140 houses a camera 13, a collimator 14, a radiation source 19, a distance sensor 27, a motion sensor 28, and an irradiation field lamp 29 in a manner similar as that of the radiation irradiating apparatus 10 of the embodiment described above. The radiation source portion 140 which swings freely is configured to be fixed at swinging positions by operating a locking lever 141.

In the radiation irradiating apparatus 100 which is configured to be movable, a photographed image G1 obtained by the camera 13 is displayed on the monitor 127 of the operating unit 125.

In the case that operations prior to imaging are performed, an operator extends the arm portion 130 and sets the length of the arm portion 130 and the swinging position of the radiation source portion 140 such that the radiation source portion 140 is positioned directly above a subject H. By photographing the subject H with the camera 13 in this state, the position of the radiation detector 30 can be specified based on the markers 34A through 34D of the radiation detector 30 included in the photographed image G1 in the same manner as in the embodiment described above.

In addition, in the case that the radiation irradiating apparatus 100 which is configured to be movable is employed, the extension of the arm portion 130, the swinging position of the radiation source portion 140, and the driving of the collimator 14 may be controlled such that the detection region and the irradiation field region which are overlapped on the photographed image G1 are matched.

Hereinafter, the operational effects of the embodiments of the present disclosure will be described.

A surface of a radiation detector that includes a detection region forms a rectangular shape. Each of a plurality of markers is provided at least at one of the vicinities of different edges and the vicinities of different corners of the surface that includes the detection region. Thereby, the possibility that a subject will cover all of the plurality of markers will be decreased. Accordingly, the probability that a photographed image will include a marker can be increased, and identifying information can be positively obtained as a result.

By identifying radiation detectors based on the identifying information, mistaken handling of radiation detectors that should be utilized can be prevented.

What is claimed is:

1. A radiation imaging apparatus, comprising:
a display; and
at least one hardware processor configured to implement:
a radiation source that emits radiation onto a subject;
a photography unit for photographing the subject to obtain a photographed image of the subject;
a radiation detector for detecting radiation which has passed through the subject and for generating a radiation image of the subject; and
an identifying information obtaining unit for detecting a marker, provided on the radiation detector, that represents identifying information of the radiation detector, the marker being provided on a side of the radiation detector that includes a radiation detecting surface, and obtaining the identifying information of the radiation detector from the marker in a case that the marker is detected,
wherein a surface of the radiation detector that includes the radiation detecting surface that detects radiation is of a rectangular shape,
wherein each of a plurality of markers is provided at least at one of a vicinities of different edges and a vicinities of different corners of the surface that includes the radiation detecting surface such that the markers define four corners of the radiation detecting surface,
wherein a surface of the radiation detector opposite of the detecting surface is provided with another marker that represents that the surface is that which is opposite of the detecting surface,
wherein the identifying information obtaining unit is configured to determine whether the another marker is in the photographed image,
wherein the at least one hardware processor is further configured to implement controlling the display to display a warning in response to determining that the another marker is in the photographed image, and
wherein the warning comprises an indication instructing a repositioning of the radiation detector.

2. The radiation imaging apparatus as defined in claim 1, wherein:
the radiation source and the photography unit are provided as an integrated unit.

3. The radiation imaging apparatus as defined in claim 1, wherein the at least one hardware processor is further configured to implement:
an identifying unit for identifying the radiation detector based on the identifying information.

4. The radiation imaging apparatus as defined in claim 1, wherein:
the marker is a bar code.

5. The radiation imaging apparatus as defined in claim 1, wherein the plurality of markers comprise a plurality of pairs of markers provided at each corner of the surface that includes the radiation detecting surface such that the pairs of markers define each corner of the radiation detecting surface.

6. The radiation imaging apparatus as defined in claim 3, wherein:
the marker is provided at a portion at the side of the detecting surface other than a detection region that detects radiation.

7. A method for controlling a radiation imaging apparatus equipped with a radiation source that irradiates radiation onto a subject and a photography unit for photographing the subject to obtain a photographed image of the subject, comprising:
detecting a marker that represents identifying information of a radiation detector that detects radiation which has passed through the subject and generates a radiation image of the subject, provided on a side of the radiation detector at the side of a radiation detecting surface, from the photographed image; and
obtaining the identifying information of the radiation detector from the marker in a case that the marker is detected,
wherein a surface of the radiation detector that includes the radiation detecting surface that detects radiation is of a rectangular shape,
wherein each of a plurality of markers is provided at least at one of a vicinities of different edges and a vicinities of different corners of the surface that includes the radiation detecting surface such that the markers define four corners of the radiation detecting surface, and
wherein a surface of the radiation detector opposite of the detecting surface is provided with another marker that represents that the surface is that which is opposite of the detecting surface,
wherein the method further comprises determining whether the another marker is in the photographed image,
wherein the method further comprises controlling a display to display a warning in response to determining that the another marker is in the photographed image, and
wherein the warning comprises an indication instructing a repositioning of the radiation detector.

8. A non-transitory recording medium having recorded therein program that causes a computer to execute a method for controlling a radiation imaging apparatus equipped with a radiation source that irradiates radiation onto a subject and a photography unit for photographing the subject to obtain a photographed image of the subject, the program comprising the procedures of:
detecting a marker that represents identifying information of a radiation detector that detects radiation which has passed through the subject and generates a radiation image of the subject, provided on a side of the radiation detector at the side of a radiation detecting surface, from the photographed image; and
obtaining the identifying information of the radiation detector from the marker in a case that the marker is detected,
wherein a surface of the radiation detector that includes the radiation detecting surface that detects radiation is of a rectangular shape,
wherein each of a plurality of markers is provided at least at one of a vicinities of different edges and a vicinities of different corners of the surface that includes the radiation detecting surface such that the markers define four corners of the radiation detecting surface, and
wherein a surface of the radiation detector opposite of the detecting surface is provided with another marker that represents that the surface is that which is opposite of the detecting surface,
wherein the program further comprises procedures of determining whether the another marker is in the photographed image,
wherein the program further comprises procedures of controlling a display to display a warning in response to determining that the another marker is in the photographed image, and wherein the warning comprises an indication instructing a repositioning of the radiation detector.

\* \* \* \* \*